United States Patent
Angerer et al.

(10) Patent No.: US 10,242,587 B2
(45) Date of Patent: Mar. 26, 2019

(54) LIMB IMMOBILIZING BRACE AND SYSTEM

(71) Applicant: AUGMENTED TECHNOLOGIES LLC, Ann Arbor, MI (US)

(72) Inventors: Alexander Angerer, Holland, MI (US); Kaywee Lian, Ann Arbor, MI (US)

(73) Assignee: AUGMENTED TECHNOLOGIES LLC, Ann Arbor, MI (US)

( * ) Notice: Subject to any disclaimer, the term of this patent is extended or adjusted under 35 U.S.C. 154(b) by 240 days.

(21) Appl. No.: 15/177,788

(22) Filed: Jun. 9, 2016

(65) Prior Publication Data

US 2016/0371997 A1   Dec. 22, 2016

Related U.S. Application Data

(60) Provisional application No. 62/180,647, filed on Jun. 17, 2015.

(51) Int. Cl.
| | | |
|---|---|---|
| *G09B 9/00* | (2006.01) | |
| *A61F 5/058* | (2006.01) | |
| *A61N 1/38* | (2006.01) | |

(52) U.S. Cl.
CPC ............ *G09B 9/003* (2013.01); *A61F 5/0585* (2013.01); *A61N 1/38* (2013.01)

(58) Field of Classification Search
CPC ................................ G09B 9/003; F41A 33/02
See application file for complete search history.

(56) References Cited

U.S. PATENT DOCUMENTS

| | | | | |
|---|---|---|---|---|
| 7,872,849 B2* | 1/2011 | Elliott, Jr. | ............... | F41A 33/02 361/232 |
| 9,033,710 B2* | 5/2015 | Quail | ......................... | F41J 5/02 434/19 |
| 9,489,857 B2* | 11/2016 | Quail | ..................... | G09B 9/003 |
| 2012/0330395 A1* | 12/2012 | Dar | ....................... | A61B 5/1038 607/149 |
| 2014/0163444 A1* | 6/2014 | Ingvarsson | ........... | A61F 5/0102 602/2 |
| 2015/0273205 A1* | 10/2015 | Dar | .......................... | A61H 3/00 607/149 |
| 2016/0144172 A1* | 5/2016 | Hsueh | ................. | A61N 1/36003 607/48 |

OTHER PUBLICATIONS

Shocking Laser Tag; Feb. 2, 2009; Shocking Fun; https://web.archive.org/web/20090202221143/http://www.shockingfun.com/Shocking_Laser_Tag_p/lazertag.htm.*

* cited by examiner

*Primary Examiner* — Sam Yao
*Assistant Examiner* — Joshua Luo
(74) *Attorney, Agent, or Firm* — Stephen T. Olson; Harness, Dickey & Pierce, P.L.C.

(57) ABSTRACT

A battle simulation system includes a limb immobilization device. The limb immobilization device is operative for immobilizing a limb of a user in response to receipt of the control signal indicating a hit to the limb of the user. The limb immobilization device may at least partially immobilize the limb. The immobilization may be voluntary or involuntary.

16 Claims, 22 Drawing Sheets

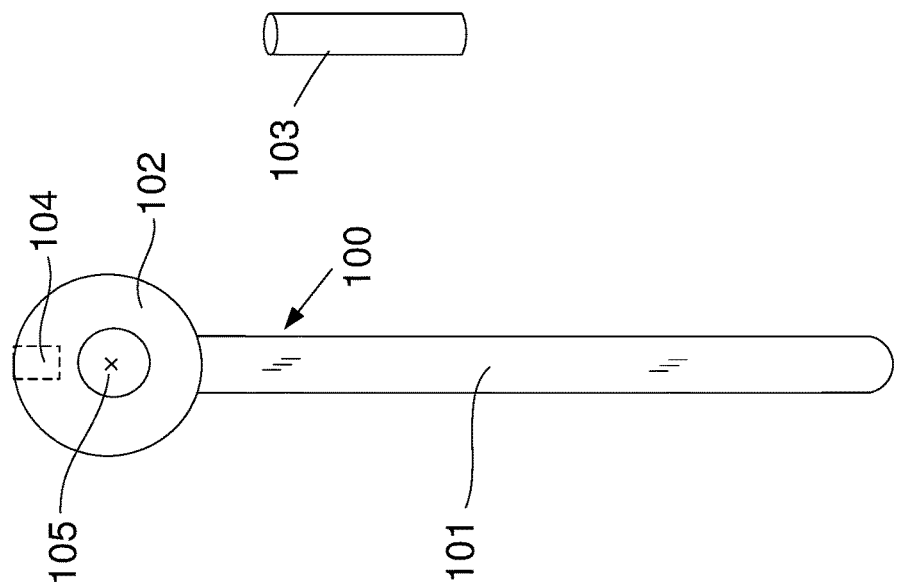
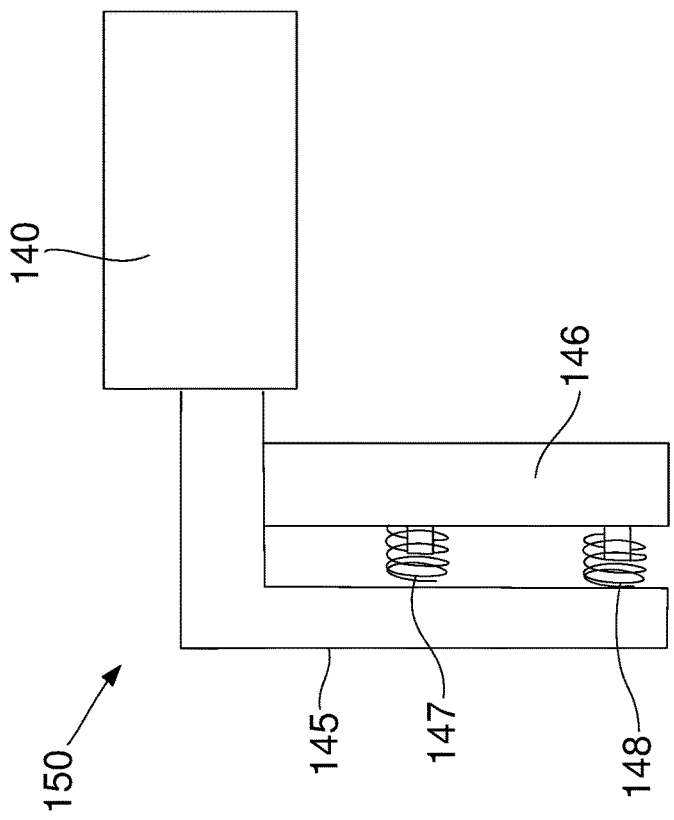

LIMB IMMOBILIZING BRACE AND SYSTEM

CROSS-REFERENCE TO RELATED APPLICATIONS

This application claims the benefit of U.S. Provisional Application No. 62/180,647, filed on 17 Jun. 2015. The entire disclosure of the above application is incorporated herein by reference.

FIELD

The present teachings generally relate to battle simulation systems. More particularly, the present teachings relate to a limb immobilizing brace and system for a battle simulation system.

BACKGROUND

Battle simulation systems are used both recreationally and for training purposes. For example, such systems are used in the military and law enforcement. These systems may include wearable modules which simulate battle conditions by, among other features, simulating a response to a "hit." One aspect of a hit is pain, which can be simulated by, for example, delivering an electrical shock to a participant in a battle situation.

While known battle simulation systems may have proven to be acceptable for their intended uses, a need for continuous improvement in the relevant art exists.

SUMMARY

The present disclosure relates generally to the field of wearable modules for battle simulation systems. More specifically, the present disclosure relates to the battle simulation systems that simulate a hit by immobilizing a limb. Immobilizing a limb includes any impairment of the movement of a limb. The immobilization may be voluntary or involuntary. For example, a limb may be voluntarily immobilized where a painful shock is delivered to a user if the user moves a corresponding joint. A limb may be involuntarily immobilized where a corresponding joint is physically prevented from articulation. The wearable module is a limb locking module including a locking mechanism. The locking mechanism may be a voluntary locking mechanism (e.g., an electric shock) or an involuntary locking mechanism (e.g., a mechanical lock device). The locking mechanism is configured to immobilize a limb in a first position in response to a signal, the signal simulating a hit.

In accordance with one particular aspect, the present teachings provide A limb immobilization device for a battle simulation system. The limb immobilization device includes an receiver and an electric shock generator. The receiver is operative for receiving a signal indicative of a hit to a limb of a user. The electric shock generator is operative to generate an electric shock and deliver the electric shock to the user upon receipt of the signal. The electric shock operates to at least partially immobilize the limb. The immobilization may be voluntary or involuntary.

In accordance with another particular aspect, the present teachings provide a method of simulating a battle. The method includes providing a limb immobilization device and attaching the limb immobilization device to a user. The method additionally includes receiving a control signal by the limb immobilization device in response to a simulated hit to the limb. The method further includes at least partially immobilizing the limb in response to receipt of the control signal. The limb is at least partially immobilized by delivering an electric shock to the user. The immobilization may be voluntary or involuntary.

BRIEF DESCRIPTION OF THE DRAWINGS

FIG. 11 illustrates an exemplary spring-based locking mechanism in accordance with the present teachings.

FIG. 12 illustrates an exemplary brace component in accordance with the present teachings, the brace component configured for use with a spring-based locking mechanism.

DETAILED DESCRIPTION

Detailed embodiments of the invention are disclosed herein. However, the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

As will become fully apparent below, the present teachings provide various embodiments of limb locking devices. The devices may function to at least partially immobilize a limb in response to a signal indicating a simulated hit to the limb. The limb locking devices may operate to at least partially immobilize the limb by restricting or immobilizing articulation of a corresponding joint of the user. In some embodiments, the limb locking device may operate to involuntarily immobilize the limb by mechanically restricting motion of the limb. In other embodiments, the limb locking device may operate to voluntarily immobilize the limb by delivering a painful shock to the user if the user articulates the corresponding joint.

Figure 1:
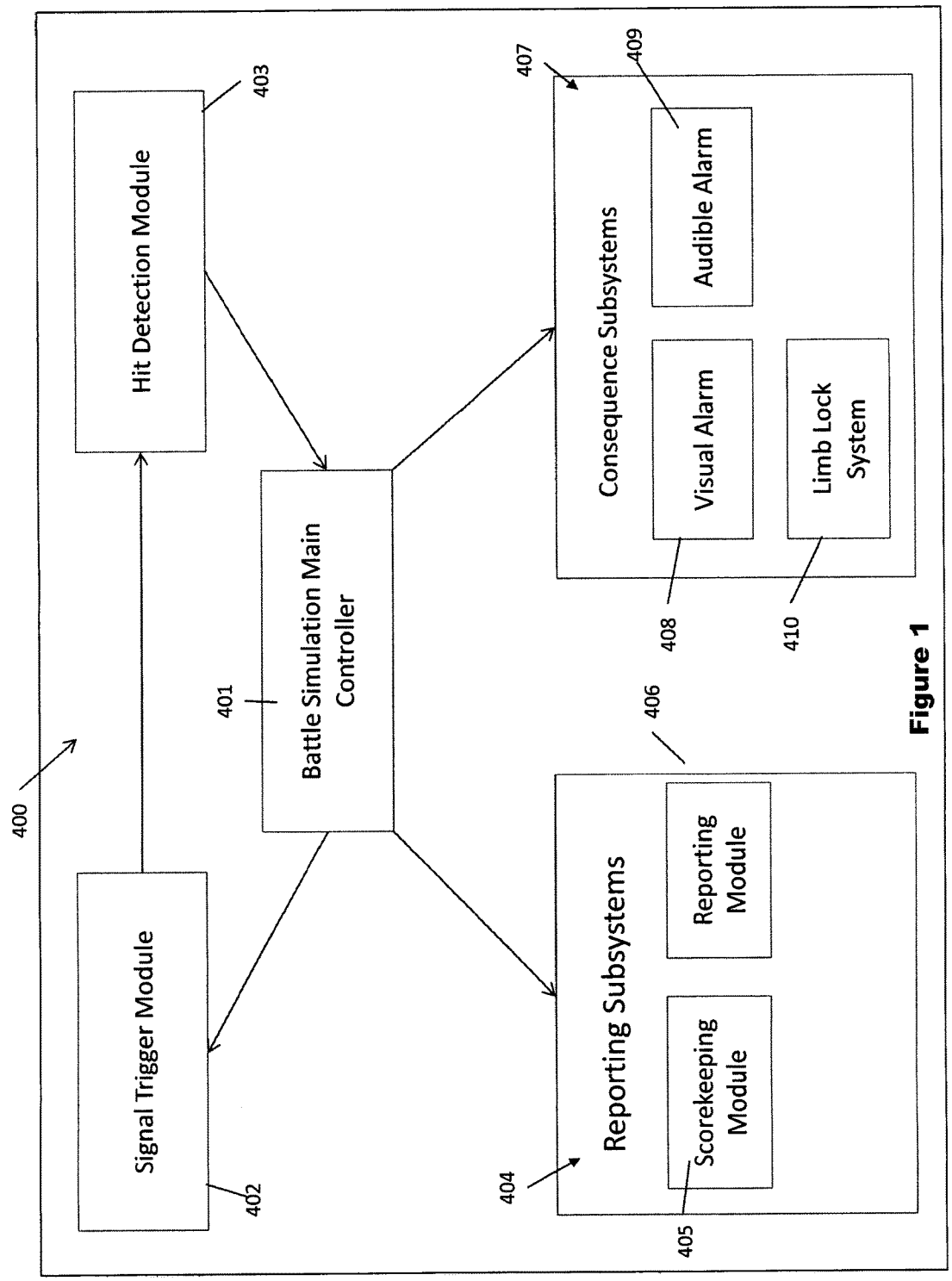
FIG. 1 schematically illustrates a battle simulation system in accordance with the present teachings, the battle field simulation system including relative position of a limb lock module within the battle field simulation system.

With initial reference to FIG. 1, an exemplary battle simulation system 400 configured in accordance with the present teachings to include a limb lock device 410 will be described. The system 400 may include other components that cooperate with the limb lock device 410 or may cooperate with conventional, commercially available components. Generally, the battle simulation system 400 may additionally include a battle simulation main controller 401 for receiving input from one or more components of the system and directing the actions of the various other components and subsystems. These components include a signal trigger module 402 operative to send a signal to engage in combat. The trigger could be, for example, simulated firing of an infrared laser embedded within, or attached to, a model firearm, the simulated fire of a vehicle mounted weapon, or a simulated explosive device. The signal could be in the form of, for example, an infrared light, a raw or processed image taken from a mounted camera, or any other suitable mechanism now known or later discovered.

The components sending input to the main controller 401 may further include a hit detection module 403 for receiving a signal generated by the signal trigger subsystem 402 and determining whether to count that signal as a hit for the context of the simulated combat. For example, if the signal sent by the signal trigger module 402 is in the form of high intensity infrared light, the hit detection module 403 may be a light sensitive panel. In certain applications, these panels may be worn by the user on various target areas, such as arms, legs, chest, and back. The infrared signals sent by the signal trigger module 402 may be encoded with information such as the identity of the weapon, the identity of the shooter, the time of firing which will allow the hit detection module 403 to determine distance, the severity of the damage, and other information.

When the hit detection module 403 detects a hit, it communicates the hit and any supplementary information to the battle simulation main controller 401. The battle simulation main controller 401 may communicate with or activate various modules and subsystems in response. These modules and subsystems may include reporting subsystems 404 and consequence subsystems 407. Reporting subsystems 404 may include a scorekeeping module 405 or a reporting module 406, alert the battle simulation combatants and supervisors of the overall progress of the simulation. Consequence subsystems 407 may alert the combatant to the detection of a hit to their person. Examples of consequence subsystems 407 may include a visual alarm module 408, an audible alarm module 409, and the limb lock system 410, as described herein. In certain applications, multiple consequence systems may be provided.

Figure 2:
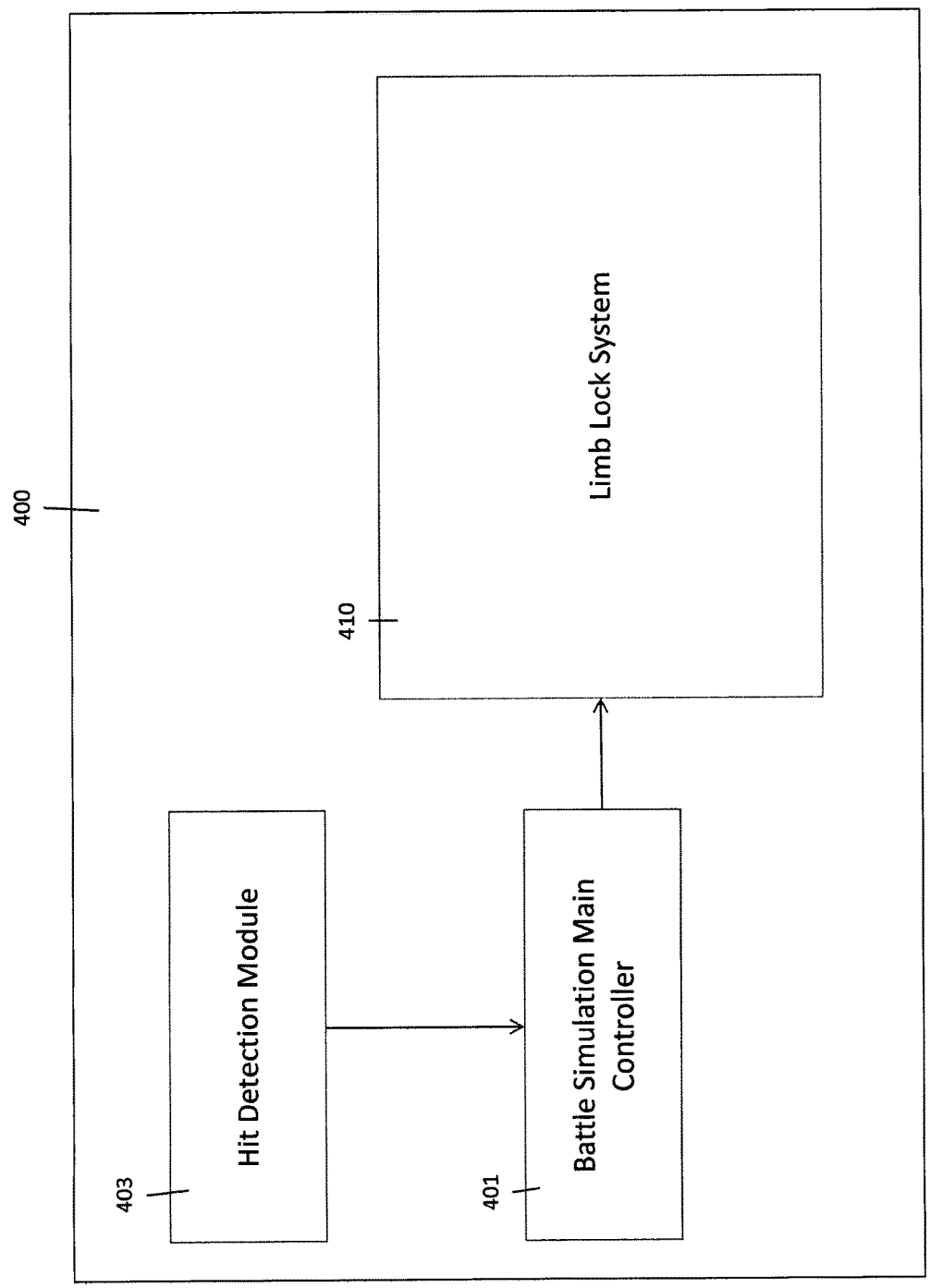
FIGS. 2-4 schematically illustrate different configurations of components within a battle simulation system in accordance with the present teachings and exemplary ways signals may travel between the components.
Figure 3:
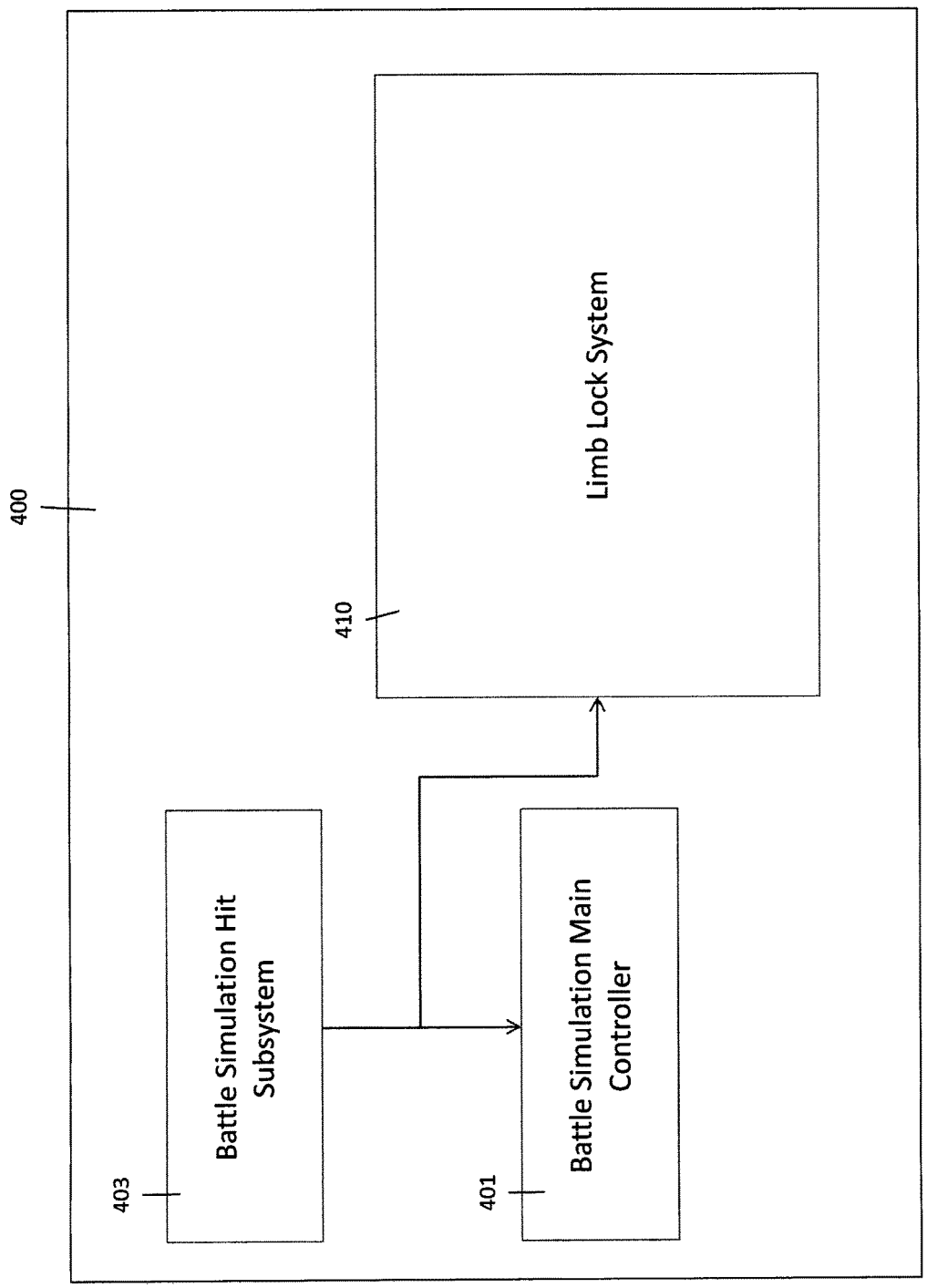
Figure 4:
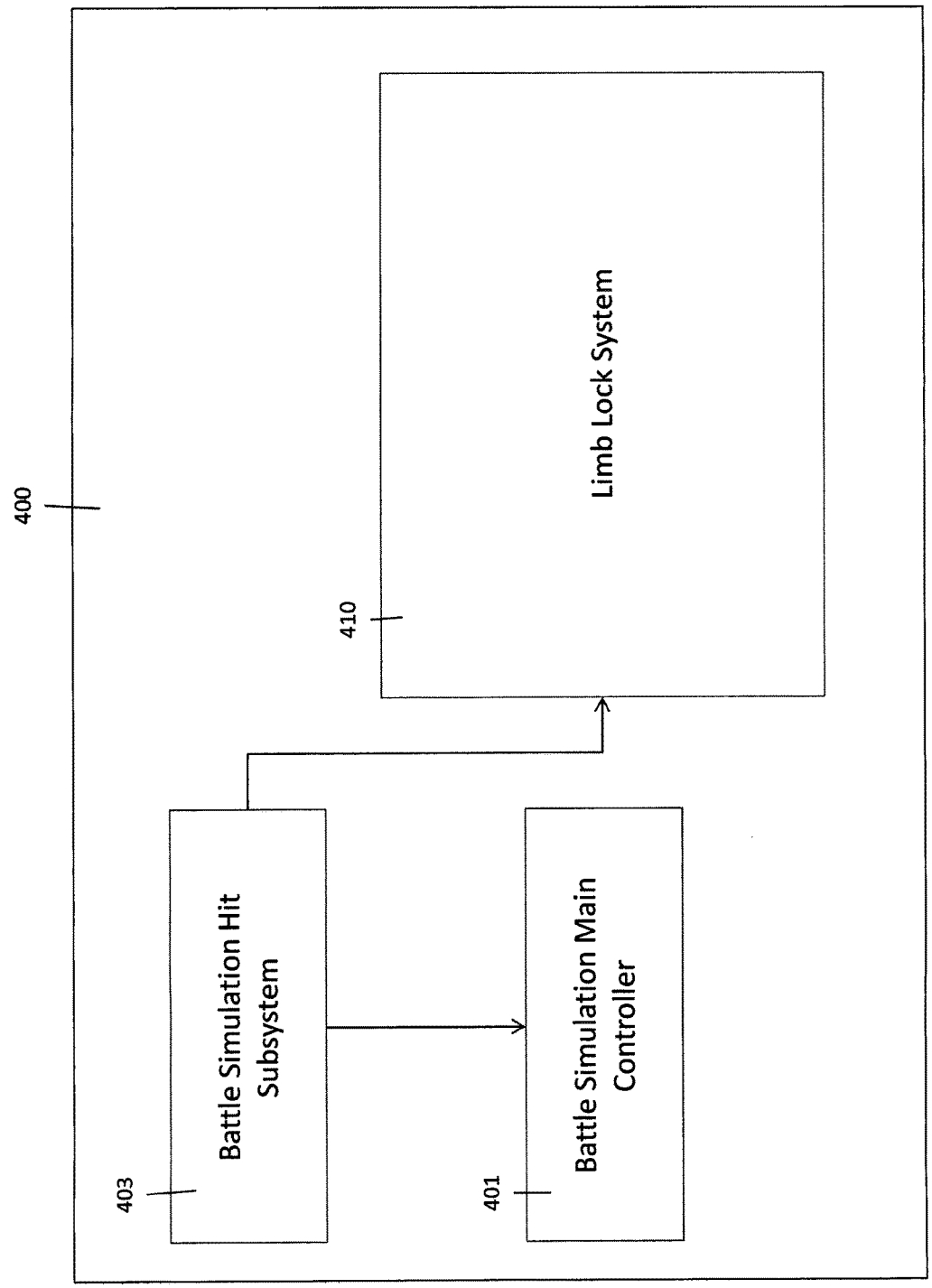
Figure 5:
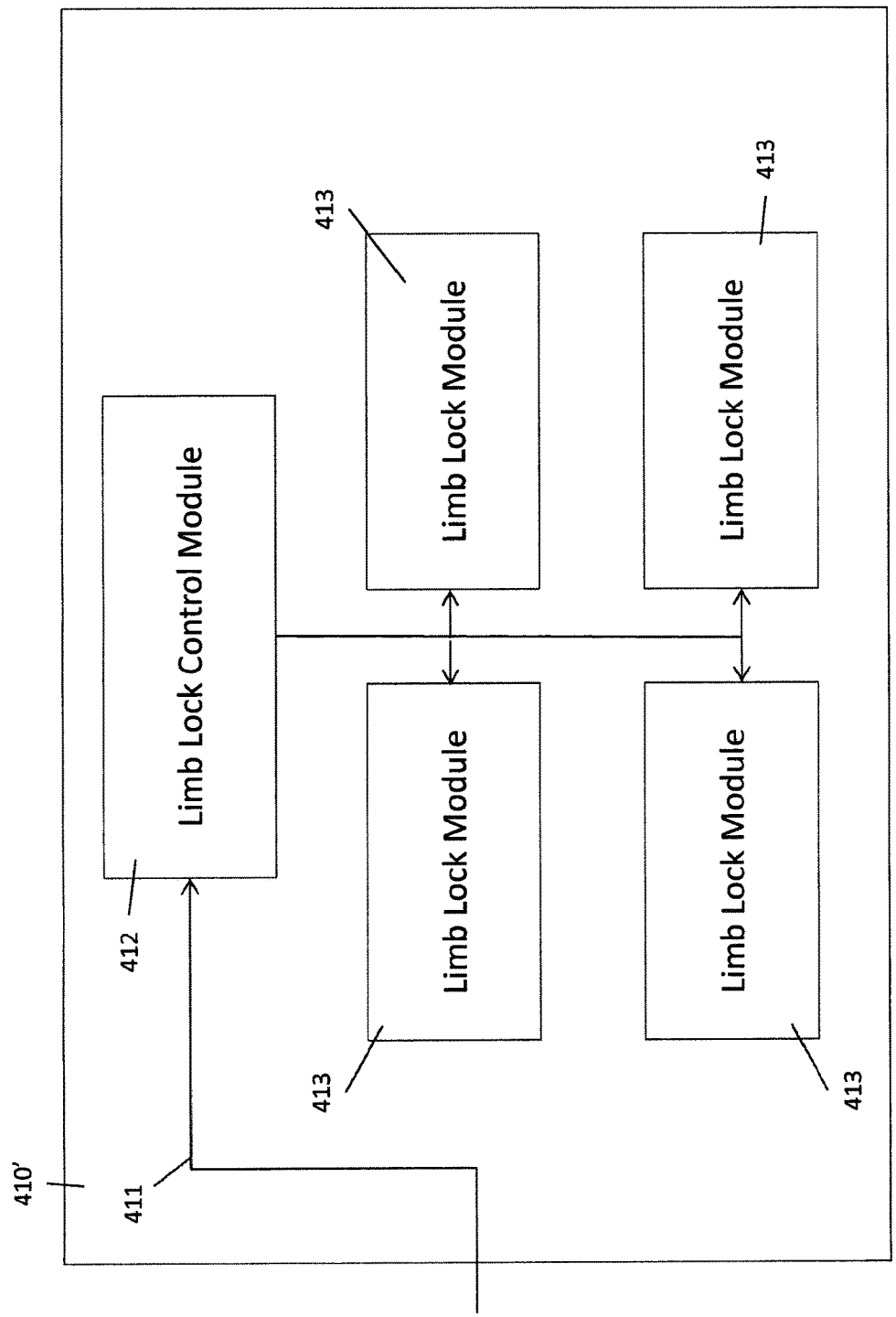
FIG. 5 schematically illustrates an embodiment of a centralized limb locking system in accordance with the present teachings.
Figure 6:
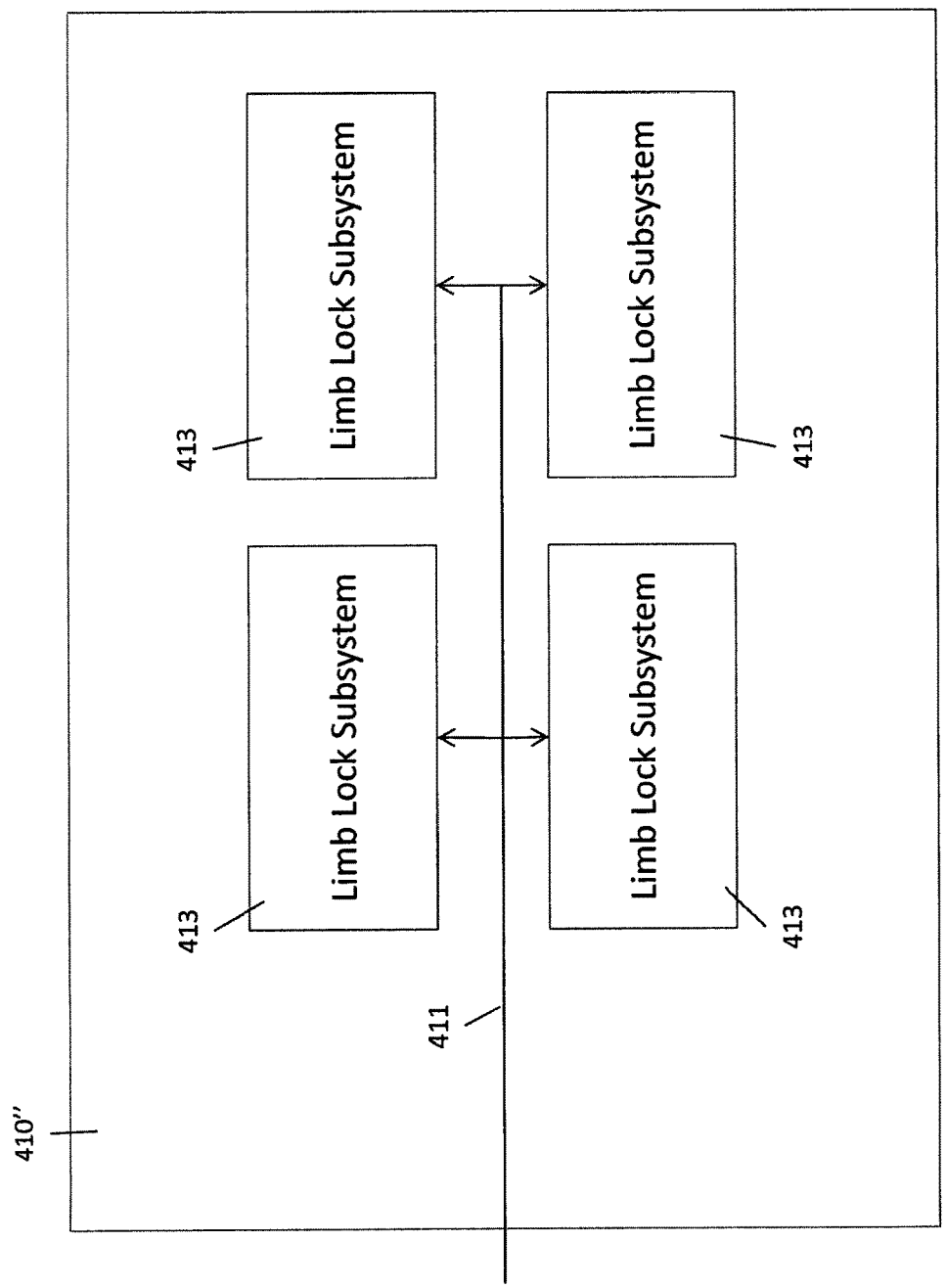
FIG. 6 schematically illustrates an embodiment of a distributed limb locking system in accordance with the present teachings.
Figure 7:
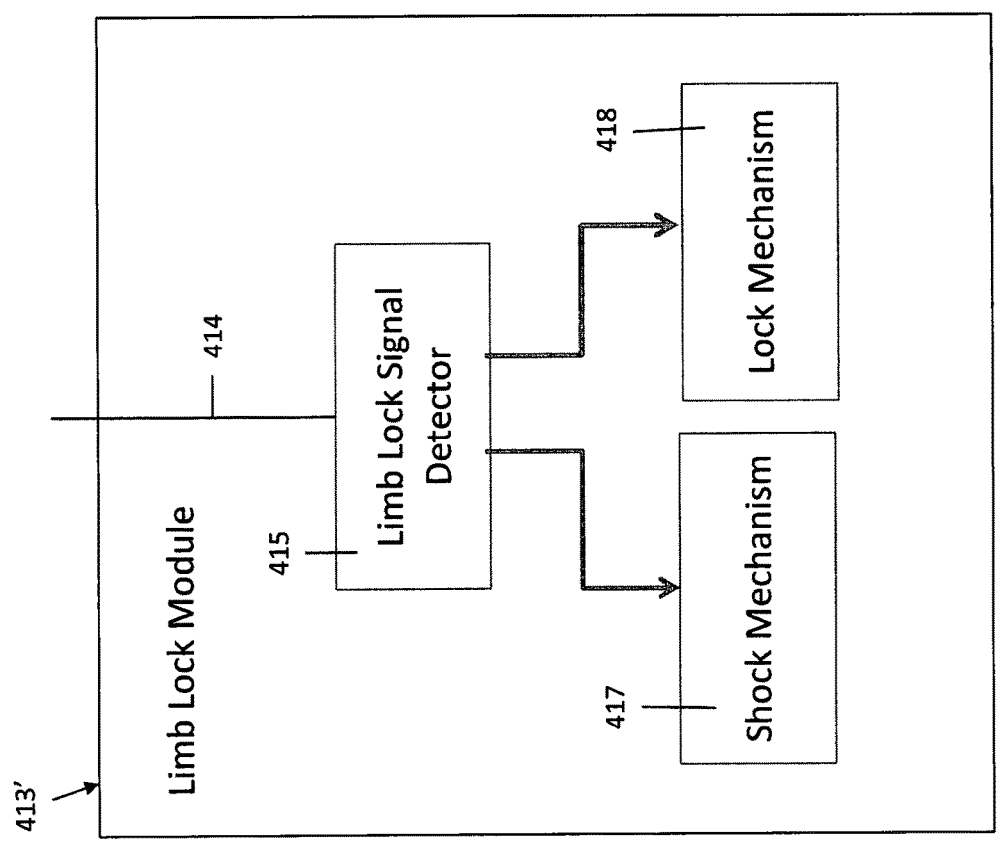
FIG. 7 schematically illustrates an embodiment of a direct limb locking module in accordance with the present teachings.
Figure 8:
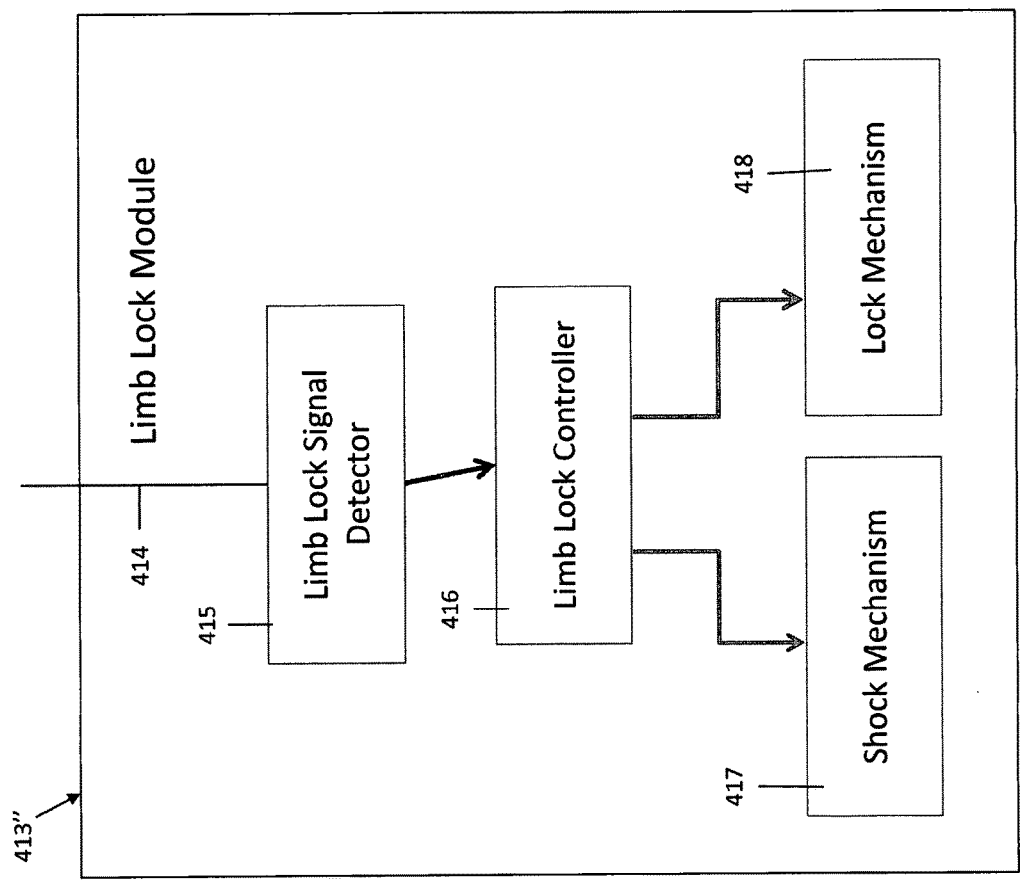
FIG. 8 schematically illustrates an embodiment of a decentralized limb locking module in accordance with the present teachings.

FIGS. 2-8 further detail configurations of components of the battle simulation system 400 and limb lock modules. FIGS. 2-4 further detail embodiments of signal passing arrangements between components of the battle simulation system 400. FIGS. 5-6 further detail embodiments of configurations representing centralized and distributed limb lock systems. FIGS. 7-8 show embodiments of configurations of individual limb lock modules associated with centralized and distributed limb lock systems.

FIGS. 2-4 show different configurations of exemplary components within a battle simulation system in accordance with the present teachings and exemplary manners of transmitting signals between the components. In FIG. 2, if the hit detection module 403 detects a hit, a signal is sent to the battle simulation main controller 401. The main controller may then send a signal to the limb lock system 410 indicating that a hit has been received. In FIG. 3, the hit detection module 403 sends simultaneous signals to the battle simulation main control 401 and the limb lock system 410. In FIG. 4, the hit detection module 403 sends a signal directly to the limb lock system 410. In the scenario in FIG. 3, the battle simulation main controller 401 may or may not receive a signal simultaneously. It will be possible in this configuration for the limb lock system 410 to function without input from the battle simulation main controller 401.

In FIG. 5, the signal 411 from one of FIGS. 2-4 enters an alternate limb lock system 410' and is received by the limb lock control module 412. The limb lock control module 412 interprets the signal 411 and may determine from the signal which and how many limbs were hit, the severity of the hit(s), and the type of weapon used. With this information, the limb lock control module signals one or several limb lock modules 413. This configuration may be called centralized because a single limb lock control module 412 controls the operations of the limb lock modules 413.

In FIG. 6, the signal 411 from one of FIGS. 2-4 enters another alternate limb lock system 410" and is received by all limb lock modules 413. In this scenario, the signal may be encoded so as to be interpreted by a limited subset of the limb lock modules. Any control information, such as the duration or severity of immobilization to be enforced, is contained in the signal itself. This configuration may be called distributed because each limb lock module 413 is responsible for interpreting and acting upon the information contained in the signal 411.

In FIG. 7, the signal 414 from one of FIGS. 5-6 enters the limb lock module 413' and is received by the limb lock signal detector 415. The signal may then be relayed to the shock mechanism 417, the lock mechanism 418, or both. This configuration may be called direct because the limb lock signal detector 415 could function without interpretation of the signal 414.

In FIG. 8, the signal 414 from one of FIGS. 5-6 enters the limb lock module 413" and is received by the limb lock signal detector 415. The limb lock signal detector 415 then relays the signal to the limb lock controller 416. The limb lock controller decodes and interprets the signal 414. The controller may then signal the shock mechanism 417, the lock mechanism 418, or both. The limb lock controller 416 may use the signal from the limb lock signal detector 415 to determine the length or severity of the shock applied by the shock mechanism 417, or the length or severity of the limb immobilization caused by the lock mechanism 418. This configuration may be called decentralized because each limb lock module 413" contains a limb lock controller 416 capable of interpreting the signal 414 and controlling the activity of the attached mechanisms.

Figure 9:
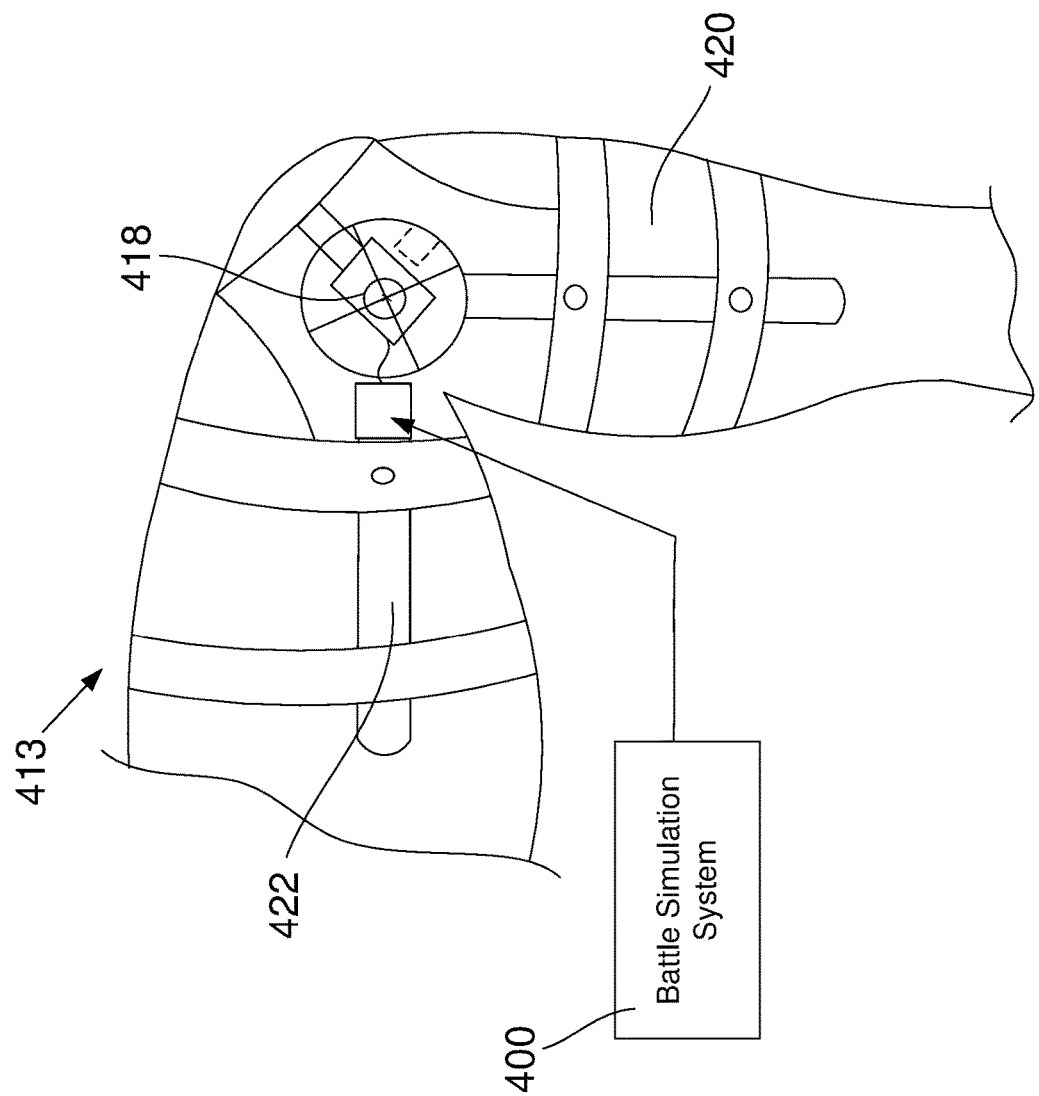
FIG. 9 schematically illustrates an example of a limb locking module within a battle simulation system in accordance with the present teachings.

FIG. 9 shows an example of a limb lock module 413 in accordance with the present teachings. As illustrated, the limb lock module 413 is specifically adapted for attachment to a leg of a user. It will be appreciated, however, that the present teachings are not so limited. On receipt of a signal from the battle simulation system 400 simulating a hit to an associated limb 420, the lock mechanism 418 may be engaged and may limit or prevent further motion in that limb 420 when the limb 420 is returned to the preset lock position. In this position, the wearer of the limb lock module 413 will not be able to bend the limb, but will still be able to maneuver the battlefield as though the limb 420 were injured. The module 413 may generally include a lock component 418 and a brace component 422 for attaching the lock component 418 to the limb 420 of the wearer.

The examples of limb lock module 413 described herein will be understood to be merely exemplary. Persons of skill in the art will understand that other methods of simulating injury, or other partial or complete immobility, may be used with battle simulation system 400 of the present teachings. For example, a shock may be designed to be painful, but not cause muscle spasms or adverse physical responses, operating at a maximum output voltage over ten-times less than a typical stun gun. After the initial shock is received, a microprocessor may send a signal down a second pathway that only shocks the user if the limb is bent past a certain angle, for example twenty degrees from a straightened position. If bent, the user's limb will complete a hidden circuit in the brace and continue to receive an electric shock periodically until the limb is returned to a straightened position. Shocking the user while bending the limb is designed to simulate the intense pain of combat injuries and the loss of limb motion through a 'voluntary' locking of the limb. This 'voluntary' locking mechanism is designed to prevent soldiers from using their limbs once shot, yet allow the user of limbs in emergency situations, such as breaking a fall. Once the system is de-activated, manually or by a second wireless signal, the wearer will be able to use their limb without inducing an electric shock.

Figure 10:
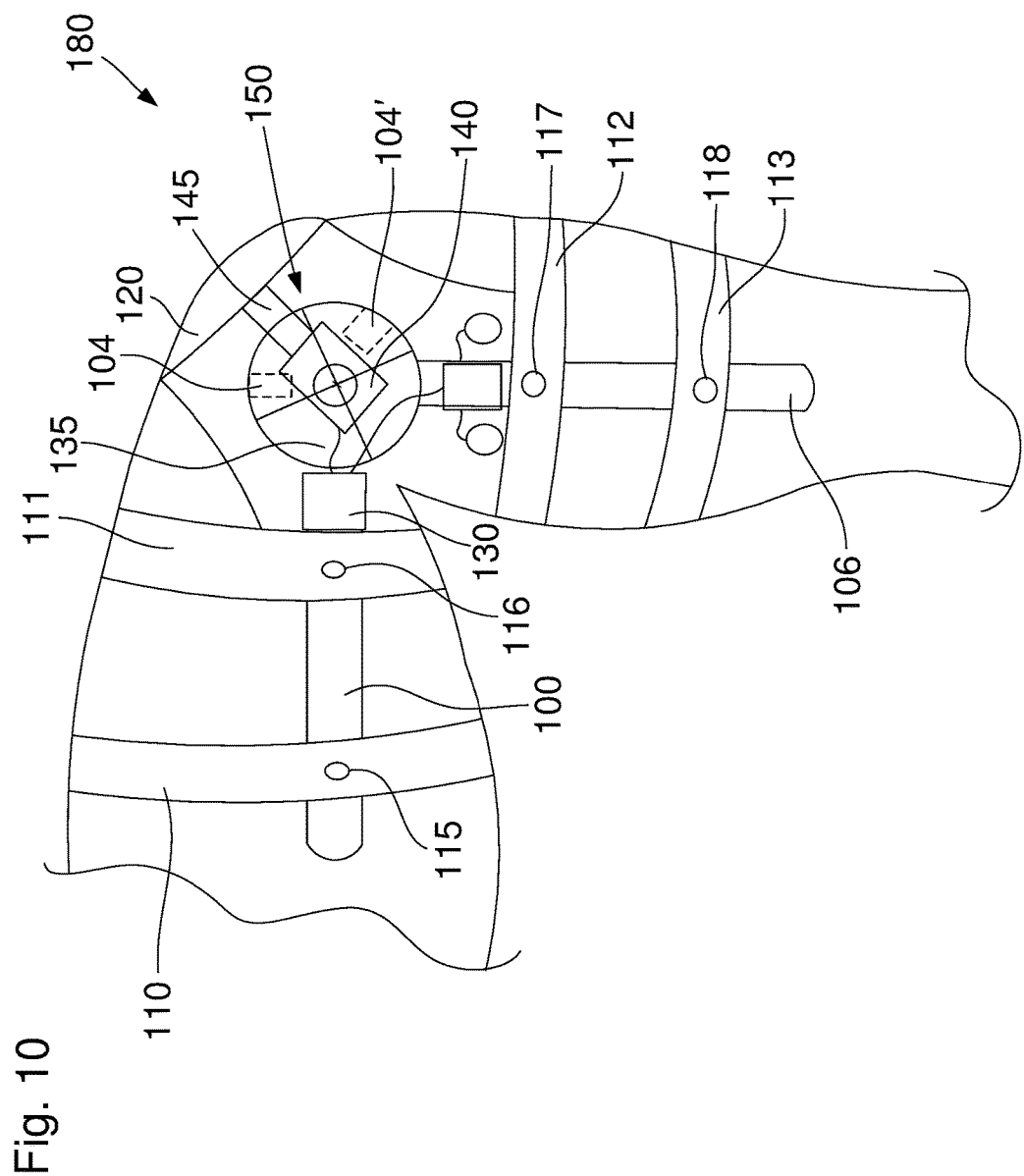
FIG. 10 illustrates an exemplary limb lock utilizing a spring-based lock attached to a user's leg in an unlocked position in accordance with the present teachings.

FIGS. 10-14 illustrate an embodiment of a limb lock module incorporating a spring-based lock. Among other advantages, this embodiment provides a simple lock that is easy to manufacture and repair. FIG. 10 shows one embodiment of the limb lock module 180. In this embodiment, the limb lock 418 is attached to a wearer's leg 420, for example. The module 180 includes two brace components 100 and 106, explained in more detail with reference to FIG. 12, and a spring-based lock or lock mechanism 150, explained in more detail with reference to FIG. 11.

FIG. 11 further illustrates the spring-based lock 150. A motor 140 may be attached to a linear actuator 145. The actuator 145, in an unlocked position rests against spring 147 and 148. These springs may press against the locking pin 146. Upon receipt of a simulated hit, the motor 140 engages, moving the linear actuator 145. This causes the springs 147 and 148 to tension against the locking pin 146. This tension causes the pin to press against the outside of the joint 102. The edges of the locking pin 146 may be rounded or smoothed to avoid damaging the components against which it rubs while under tension. When the user returns his limb to the locked position after receiving a simulated hit, the locking pin 146 presses into the slot 104 immobilizing the joint 102 and limb lock module 413 as a whole.

FIG. 12 further details a brace component 100 including a bar 101 attached to a joint 102. The joint 102 has a cavity 105 into which a pin 103 is inserted allowing the joint 102 to rotate. The joint 102 also has a slot 104 into which fits the locking pin 146 in FIG. 8. The position of the slot 104 on the joint 102 determines the locked position of the joint 102 and the limb lock module 413 as a whole. By adjusting the position of the slot, the locking position of the limb lock module 413 can be adjusted for comfort and safety.

As shown in FIG. 10, the brace component 100 may be paired with a similar mate 106 with a slot 104 positioned to meet with the mate's slot 104' when the leg 420 reaches the locked position. Because the locked position in this embodiment is straight, and the wearer's leg is bent, the slots 104 and 104' are misaligned. Straps 110, 111, 112, and 113 wrap around the wearer's leg to secure the limb lock module. The straps 110, 111, 112, and 113 in this embodiment are elastic bands and are secured to the brace part 100 with fasteners 115, 116, 117, and 118. The fasteners 115, 116, 117, and 118 in this embodiment are button clasps. Any suitable mechanism, now known or later discovered, may be used to secure the limb lock module 180 to the wearer's leg, such as an elastic sleeve, hook-and-eye fasteners, or being sewn to the brace component. A kneepad 120 may also be attached to the module 180 to replace protective gear commonly worn during battle simulation training.

Figure 13:
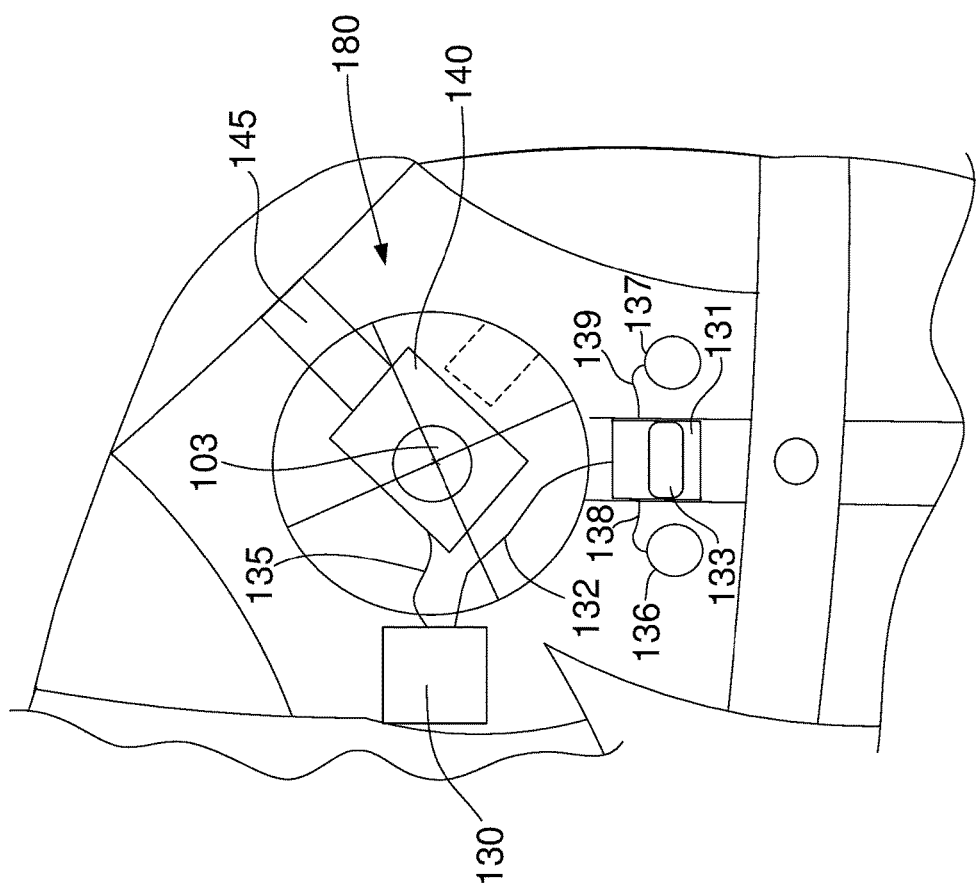
FIG. 13 illustrates an exemplary limb locking device in accordance with the present teachings, the limb locking device utilizing a spring-based lock attached to a user's leg in an unlocked position.

FIG. 13 shows a detail view of the limb lock module 180 from FIG. 10. A wireless receiver 130 may be electrically connected by wire 135 to the motor 140. The wireless receiver 130 may contain circuitry configured to receive a control signal from the main controller 401 or otherwise detect a simulated hit signal and activate the motor 140. The actuator 145 and motor 140 may sit on top of the pin 103 to allow free motion of the joint 102 without impeding its locking function. An electronic circuit 131 is attached by wire 132 to the wireless receiver 130. Upon receiving and decoding a signal from the wireless receiver 130, the electronic circuit 131 may operate to create a high voltage shock using a transformer 133. The high voltage shock is then transmitted to the user through electrodes 136 and 137 attached by wires 138 and 139.

Figure 14:
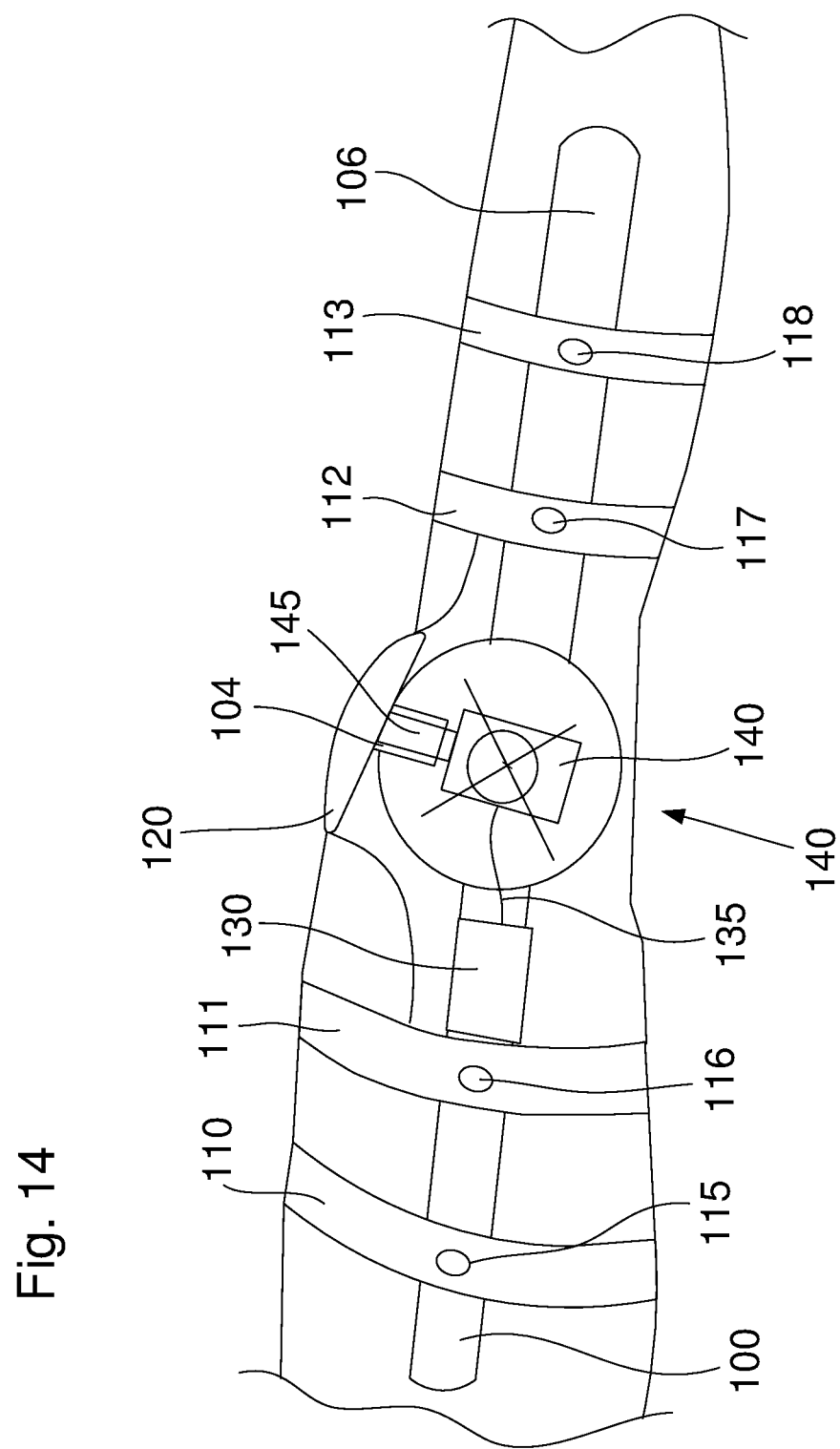
FIG. 14 illustrates an exemplary limb locking device in accordance with the present teachings, the limb locking device utilizing a spring-based lock attached to a user's leg in the locked position.

FIG. 14 shows the limb lock module 180 from FIG. 10 in its locking position. The motor 140 has been engaged and the locking pin 146 has been pressed into the slots 104 and 104', which are aligned. To disengage the limb lock module, upon a signal from the wireless receiver 130, the motor 104 is reversed, pulling the locking pin 146 from slots 104 and 104'.

FIGS. 15-18 show another embodiment of a limb lock module 546. In this embodiment, the limb lock module 546 includes a spring and linear actuator based lock. Among other advantages, this embodiment utilizes few external components. This allows the lock to be lightweight and reduces possible unwanted interference with the movement of the wearer and realism of the simulation. On receipt of a signal from the battle simulation system 400 simulating a hit to the limb 420, the lock 418 is engaged and will prevent further motion in that limb when the limb 420 is returned to the preset lock position. In this position, the wearer of the limb lock 413 will not be able to bend the limb, but will still be able to maneuver the battlefield as though the limb were injured.

Figure 15:
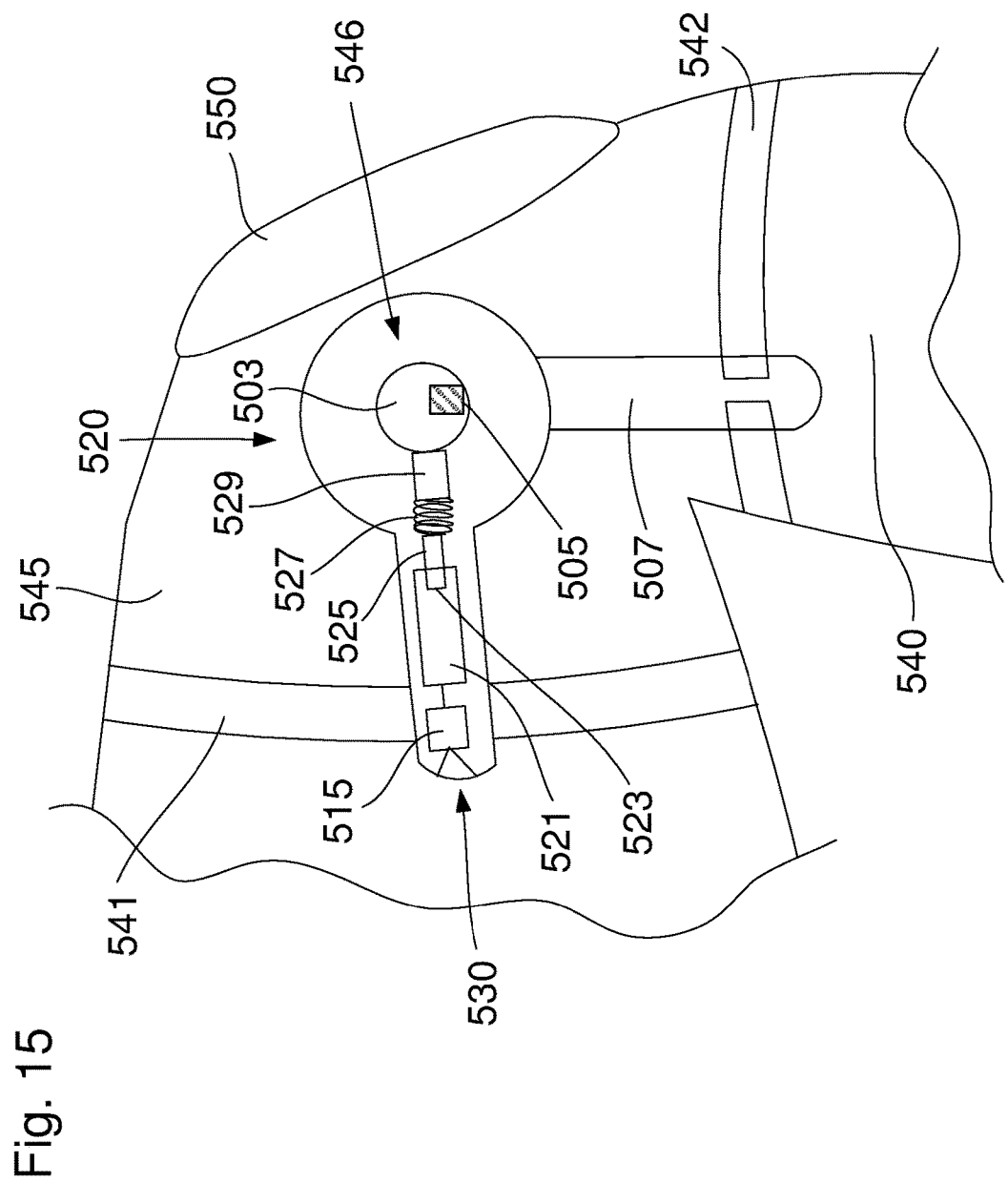
FIG. 15 illustrates an exemplary limb locking module in accordance with the present teachings, the limb locking module utilizing an internal spring-based lock in an unlocked position.

FIG. 15 shows the limb lock module 546 in an unlocked position. The embodiment includes a lower brace component 507, explained in more detail in FIG. 16, and an upper brace component 520, explained in more detail in FIG. 17 which are attached to the wearer. Built into the upper brace component 520 is a linear actuator 530, forming the active portion of the locking mechanism.

Figure 16:
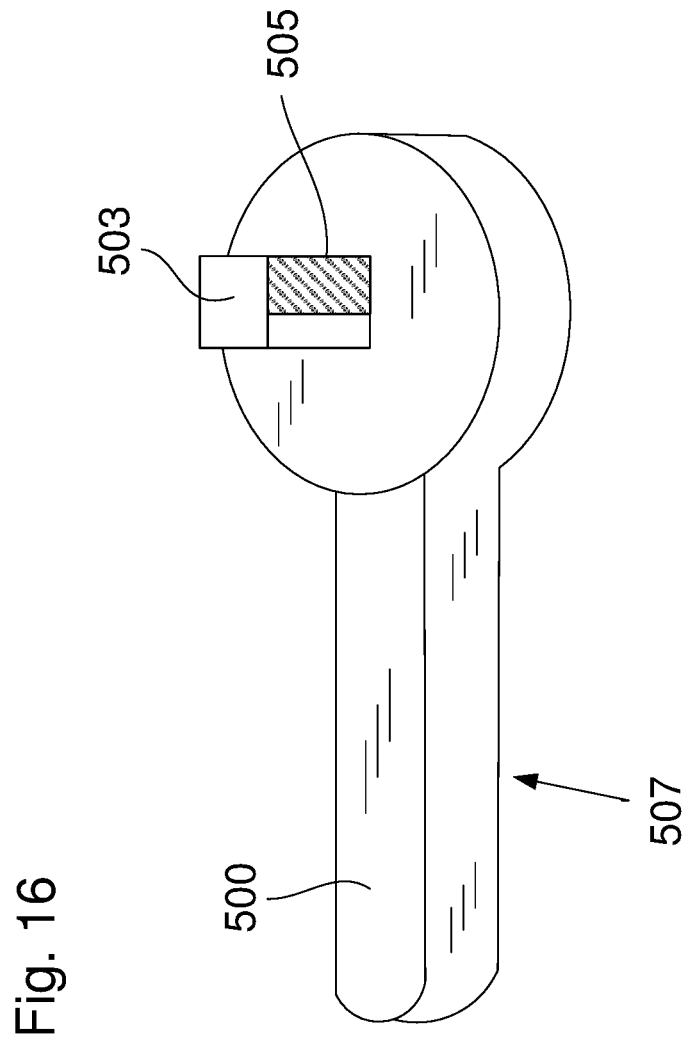
FIG. 16 illustrates an exemplary brace component in accordance with the present teachings, the brace component configured for use with an internal spring-based lock.

FIG. 16 further illustrates the lower brace component 507. The lower brace component 507 includes a brace 500 and a fixed pin 503. The fixed pin 503 has a cavity 505 into which the locking pin 529 will fit. In one embodiment, the brace component 507 is machined from a single piece of material to reduce the risk of the fixed pin 503 becoming dislodged.

Figure 17:
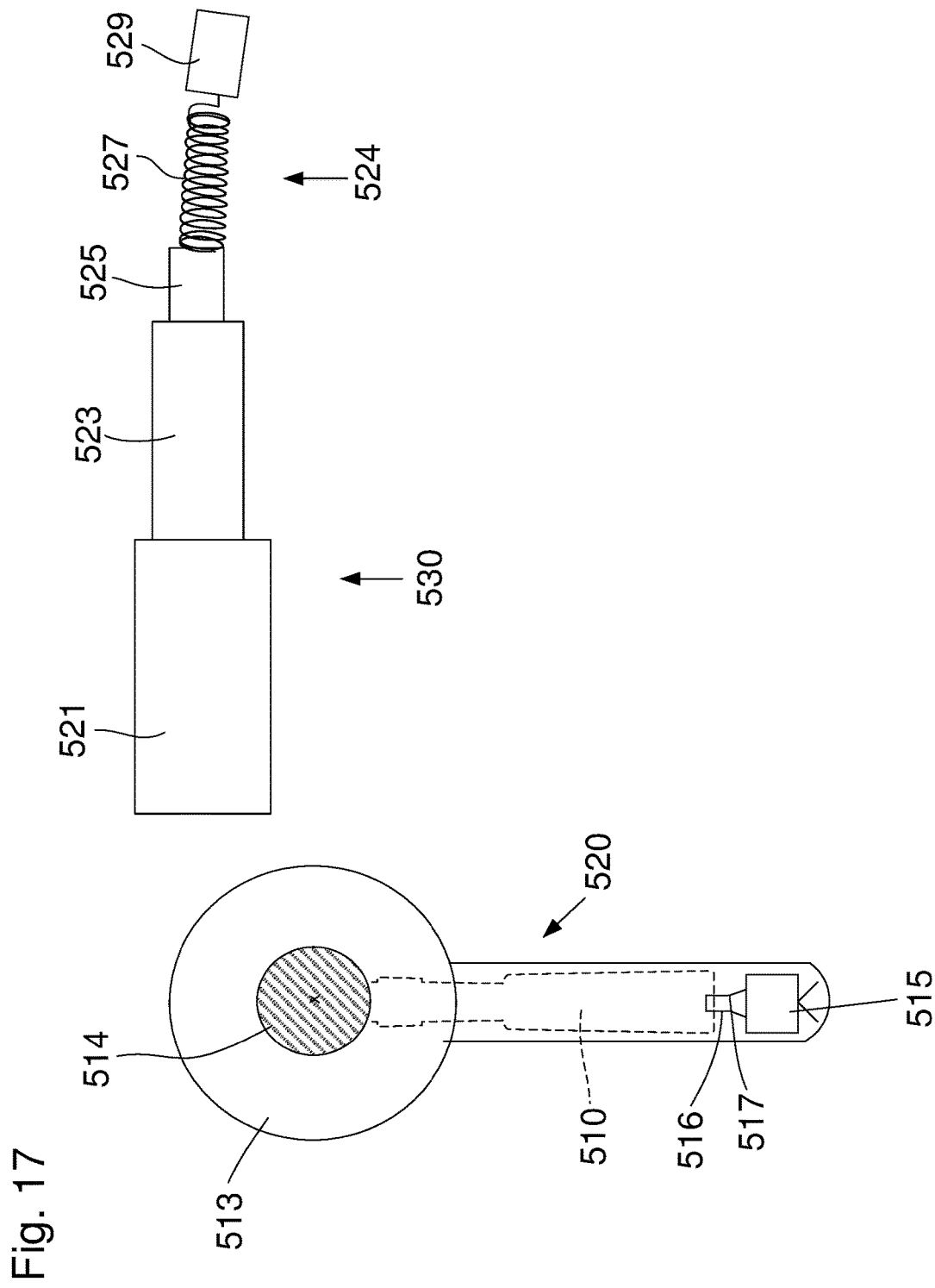
FIG. 17 illustrates another exemplary brace component in accordance with the present teachings, the brace component configured for use with an internal spring-based lock.

FIG. 17 further illustrates the upper brace component 520 that mates with the lower brace component 507. The upper brace component 520 includes a body piece 513 that is shaped to allow for a cavity 514 which fits the fixed pin 503. The body piece 513 is also large enough to provide for a cavity 510 into which the linear actuator 530 will fit. The upper brace component 520 also includes a wireless signal receiver 515 connected by wires 516 and 517 through the body piece 513 to the linear actuator 530. The linear actuator 530 is comprised of a motor 521 attached to a piston 523. The piston is attached to a separated locking pin 524 which includes a pin 525 attached by spring 527 to the locking pin 529. The spring force of the spring 527 is determined based on factors including the size of the linear actuator 530 and upper brace component 520.

As shown in FIG. 15, the two brace components 507, 520 may be secured by elastic bands 541 and 542 as well as an elastic mesh covering 545. The mesh covering 545 may cover the brace components 520 and 507 to protect from accidental damage. The upper brace component 520 rotates about the fixed pin 503 of the lower brace component 507. The elastic mesh covering 545 is also attached to a protective knee pad 550.

Because the limb lock module 546 is in an unlocked position, the cavity 505 and locking pin 529 are misaligned. On receipt of a signal, the wireless signal receiver 515 triggers the motor 521 activating the piston 523. The spring 527 is compressed, allowing the locking pin 529 to press against the wall of the fixed pin 503. When the wearer reaches the lock position the locking pin 529 slides into the cavity 505 preventing the rotation of the upper brace component 520 about the fixed pin 503. The signal may also trigger an electrical shock component, as described above, or any other suitable mechanism now known or later discovered.

Figure 18:
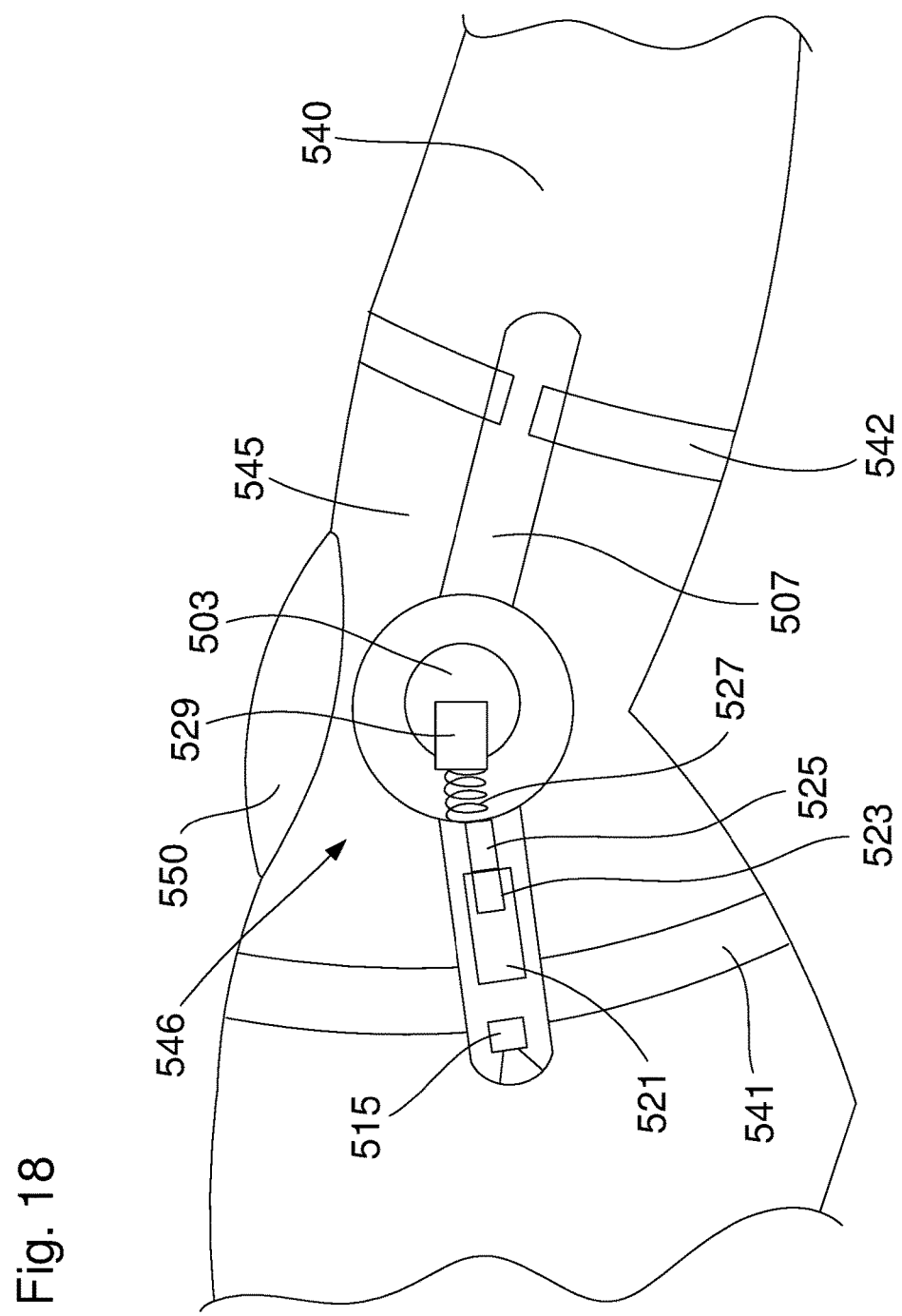
FIG. 18 illustrates an exemplary limb locking module in accordance with the present teachings, the limb locking module utilizing an internal spring-based lock in the locked position.

FIG. 18 shows the limb lock module 546 of FIG. 15 in its locked position. The locking pin 529 is pressed into the cavity 505 and held in place by the spring 527. To disengage the lock when a signal to unlock is received by the wireless receiver 515, the motor 521 activates causing the piston 523 to retract. This allows the spring 529 to expand slightly and pulls the locking pin 529 out of the cavity 505.

FIGS. 19-22 further detail an example of a limb lock module 250 that uses an electromagnetic-based lock. Among other advantages, this embodiment is lightweight and largely self-contained. The impact on the wearer may be reduced when compared to the spring-based lock discussed above. On receipt of a signal from the battle simulation system 400 simulating a hit to the limb 420, the lock 418 is engaged and will prevent further motion in that limb when the limb is returned to the preset lock position. In this position, the wearer of the limb lock 413 will not be able to bend the limb, but will still be able to maneuver the battlefield as though the limb were injured.

Figure 19:
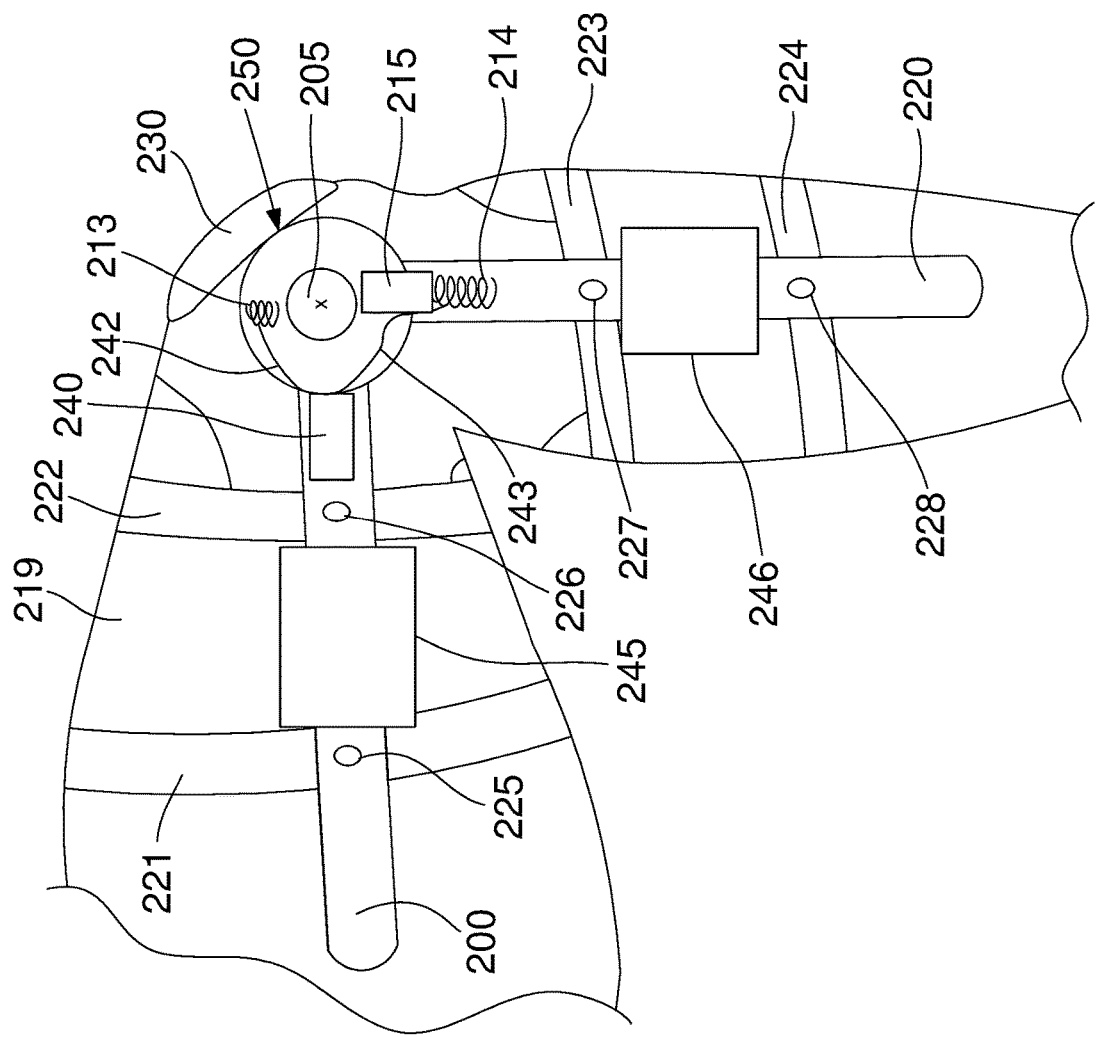
FIG. 19 illustrates an exemplary limb locking device in accordance with the present teachings, the limb locking device utilizing an electromagnetic-based lock attached to a user's leg in an unlocked position.

FIG. 19 further shows the electromagnetic-based embodiment of the limb lock module 413. The module includes an upper brace part 210 explained in more detail in FIG. 20, and a lower brace part 220, explained in more detail in FIG. 21.

Figure 20:
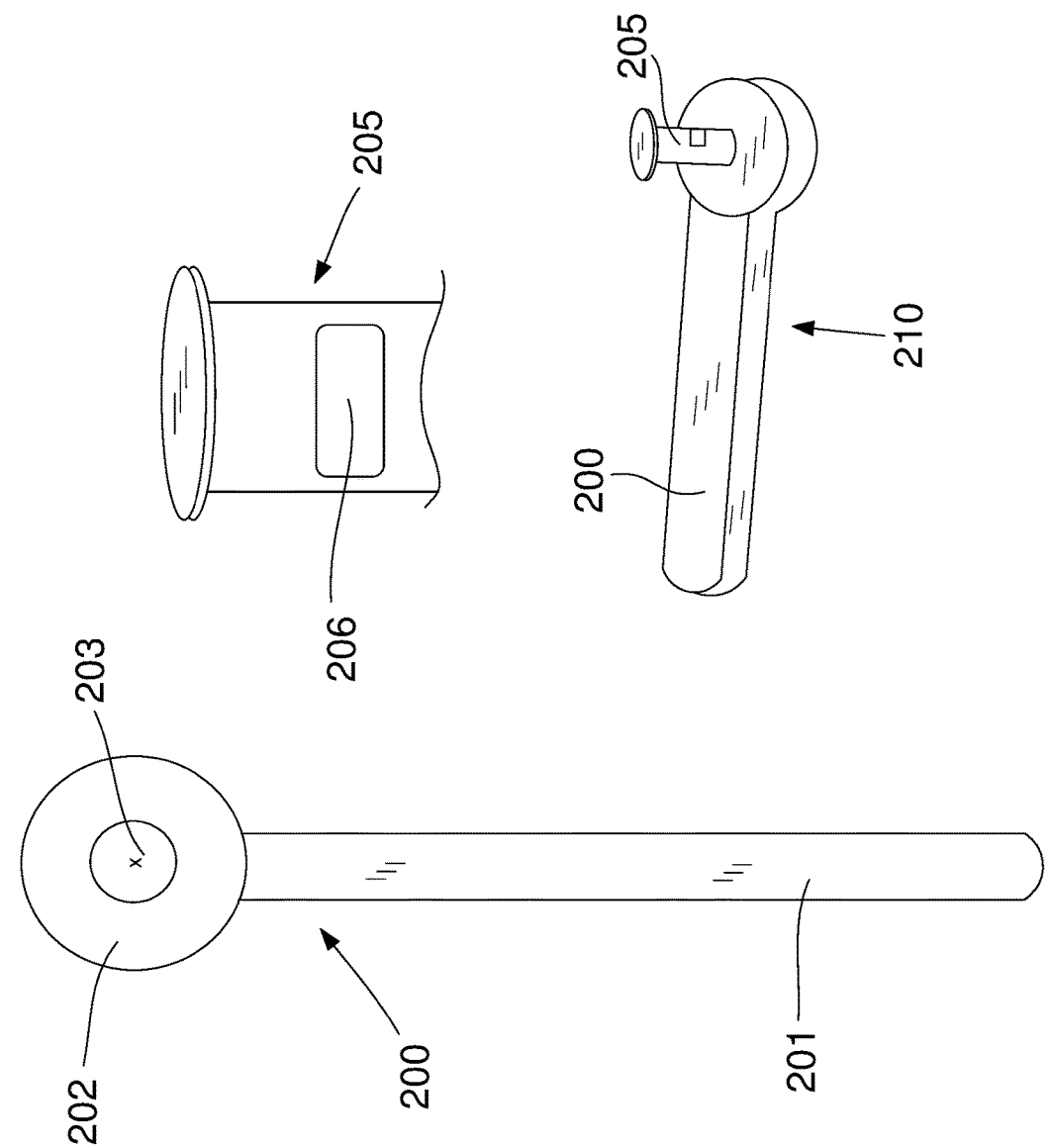
FIG. 20 illustrates an exemplary brace component in accordance with the present teachings, the brace component configured for use with an electromagnetic-based lock.

FIG. 20 shows a component of a limb lock based on an electromagnetic lock. In this embodiment, the upper brace part 210 consists of a straight brace 200 and pin 205. The straight brace 200 consists of a straight bar 201 attached to a joint 202. The joint 202 has a cavity 203 into which fixed pin 205 is inserted and fixed. The pin 205 includes a cavity 206 into which fits the magnetized locking pin 215.

Figure 21:
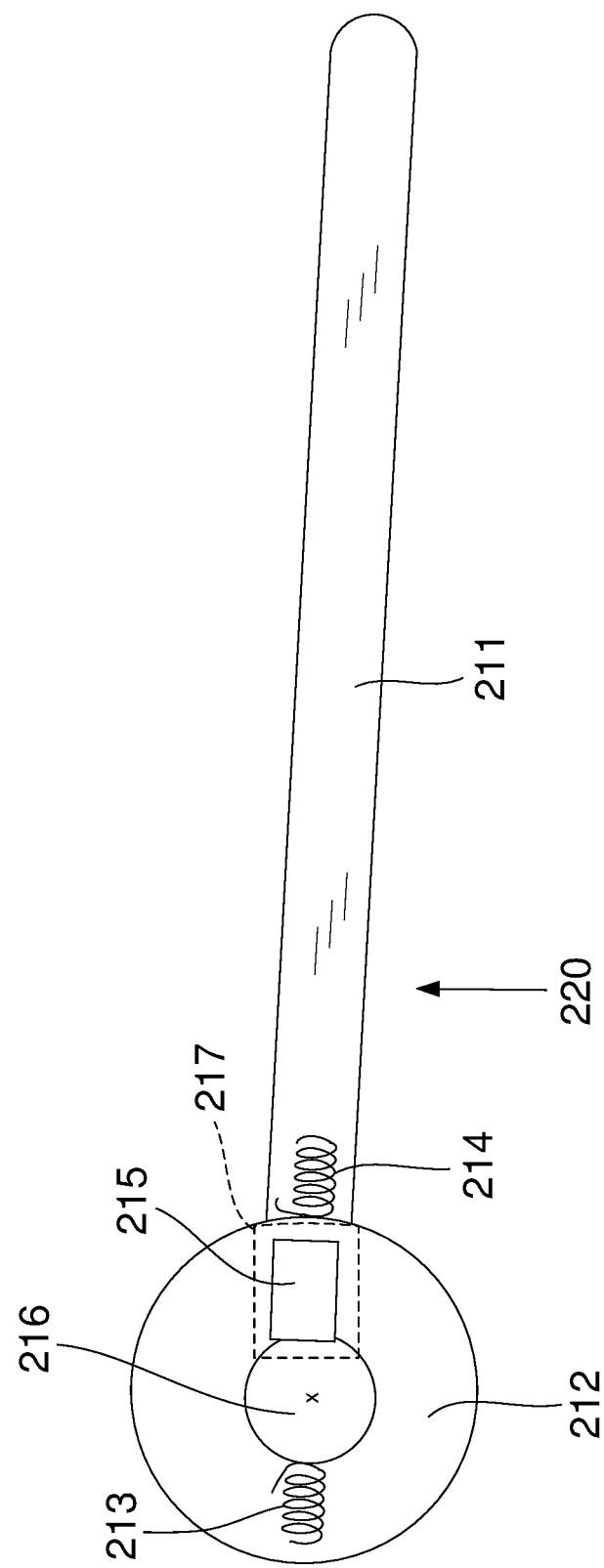
FIG. 21 illustrates another exemplary brace component in accordance with the present teachings, the brace component configured for use with an electromagnetic-based lock.

FIG. 21 shows a lower brace part 220 to mate with the upper brace part 210. This lower brace part includes a straight bar 211 attached to a joint 212 with a cavity 216. Embedded in the lower brace part are electromagnets 213 and 214 as well as a channel 217 through which the magnetized pin 215 may travel.

As shown in FIG. 19, the upper brace parts 210 and lower brace part 220 is attached to a wearer's leg 219. In this figure the leg 219 is bent, and the lock is in an unlocked position. The upper brace part 210 is paired with a lower brace part 220. Because the locked position in this embodiment is straight, and the wearer's leg is bent, the cavity 206, the channel 217, and the magnetized pin 215 are misaligned.

Straps 221, 222, 223, and 224 wrap around the wearer's leg to secure the limb lock module. The straps 221 and 222 in this embodiment are elastic bands and are secured to the upper brace part 200 with fasteners 225, 226. The straps 223 and 224 in this embodiment are elastic bands and are secured to the lower brace part 220 with fasteners 227, 228. The fasteners in this embodiment are button clasps. Any suitable mechanism, now know or later discovered, may be used to secure the limb lock module to the wearer's leg, such as an elastic sleeve, hook-and-eye fasteners, or being sewn to the brace component. A kneepad 230 is attached to the module to replace protective gear commonly worn during battle simulation training. Light sensitive panels 245 and 246 are attached to the braces 200 and 220. The panels are an embodiment of the hit detection module 403 as shown in FIG. 1. The panels will detect focused light of a predetermined wavelength, as distinct from ambient light, and communicate detection of a hit to the battle simulation to the signal receiver 240.

A signal receiver 240 is attached by wire 242 to electromagnet 213 and by wire 243 to the electromagnet 214. The signal receiver 240 contains circuitry configured to detect a simulated hit signal from light sensitive panels 245 and 246 and control the polarity of electromagnets 213 and 214. When unlocked, the polarity of the electromagnet 214 is set opposite the polarity of the end of the magnetized locking pin 215 closest to it. This causes the electromagnet 214 to attract the magnetized locking pin 215. At the same time, the polarity of electromagnet 213 is set to match the polarity of the end of the magnetized locking pin 215 closest to it. This causes the electromagnet 213 to repel the magnetized locking pin 215.

Figure 22:
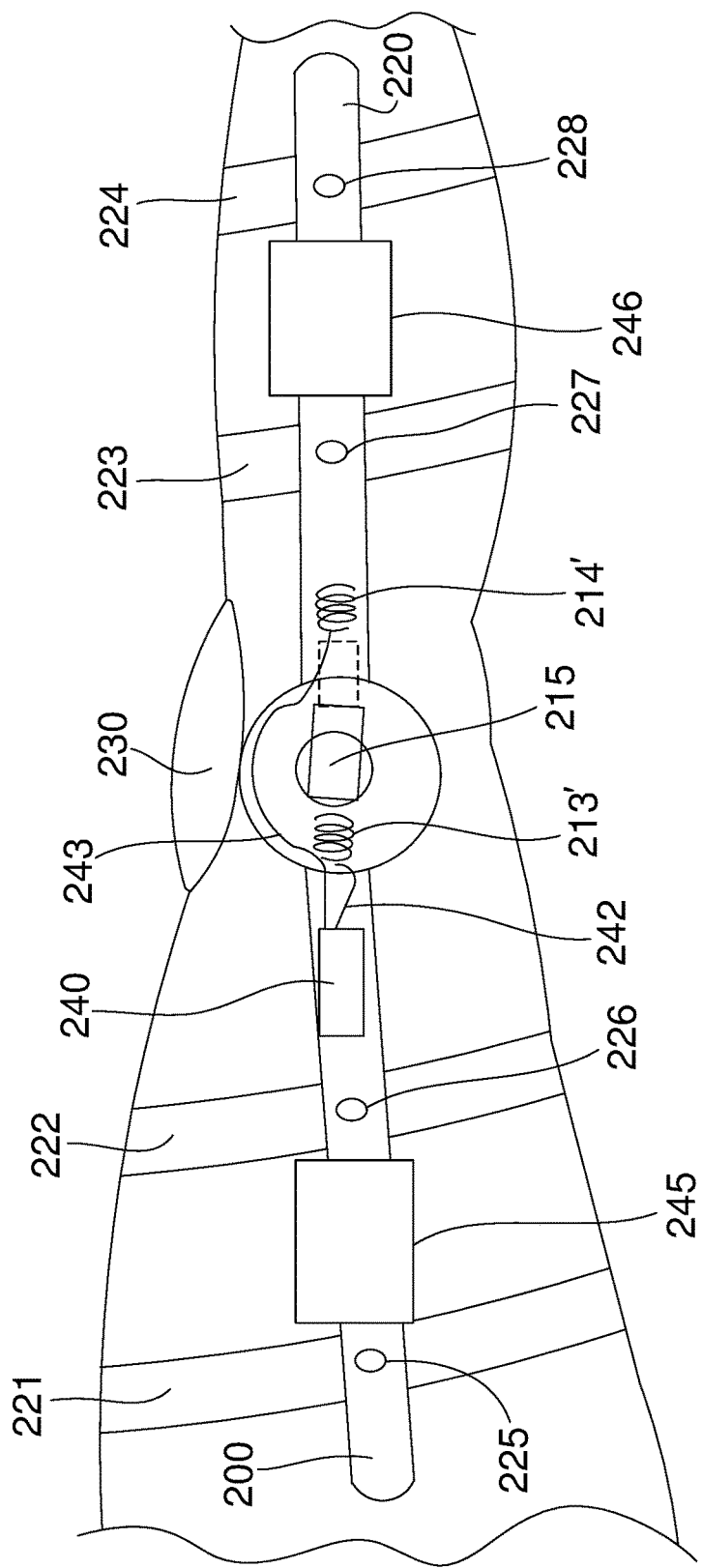
FIG. 22 illustrates an exemplary limb locking device in accordance with the present teachings, the limb locking device utilizing an electromagnetic-based lock attached to a user's leg in the locked position.

FIG. 22 shows the embodiment of the limb lock module of FIG. 19 in its locking position. The signal receiver 240 has received a simulated hit signal and the locking function has been engaged. The polarity of electromagnet 214' is set to match the polarity of the end of the magnetized locking pin 215 closest to it. This causes the electromagnet 214' to repel the magnetized locking pin 215. The polarity of electromagnet 213' is set to opposite the polarity of the end of the magnetized locking pin 215 closest to it. This causes the electromagnet 213' to attract the magnetized locking pin 215. Because the wearer has straightened his leg to reach the locking position, the channel 217 and cavity 206 of fixed pin 205 are aligned. This allows the magnetized locking pin 215 to slide into the cavity 206 of the fixed pin 205 and prevent the rotation of the joint 202. This has the effect of immobilizing the leg of the wearer.

To disengage the lock and allow the wearer use of the leg again, the polarity of electromagnet 214' is set to opposite the polarity of the end of the magnetized locking pin 215 closest to it. This causes the electromagnet 214' to attract the magnetized locking pin 215. At the same time, the polarity of electromagnet 213' is set to match the polarity of the magnetized locking pin 215 closest to it. This causes the electromagnet 213' to repel the magnetized locking pin 215. Because the channel 217 and cavity 206 of fixed pin 205 are already aligned, the magnetized locking pin 215 may slide into channel 217 and is held in place by the effects of the polarities of electromagnets 213 and 214 which allows free rotation of joint 202.

Battle simulation system 400 may be used as a stand-alone training system, or in connection with other systems, now known or later discovered. For example, battle simulation system 400 may be used in accordance with the present teachings along with the Multiple Integrated Laser Engagement System (MILES) and other laser engagement training systems. In addition, battle simulation system 400 could be used with virtual, game, or shoot house training technology.

The above embodiments, for example the spring-based embodiments and the electromagnetic-based embodiment, are demonstrated in the context of a brace worn about the wearer's knee. This is not meant to limit the application of those embodiments or the limb lock module. With slight modification, the embodiments can be adapted to perform a similar locking function on any joint on the body, including but not limited to the elbow, wrist, ankle, torso, or neck.

Battle simulation system 400 could also be configured in accordance with the present teachings to be worn over elbow and knee joints. For example, battle simulation system 400 could be integral with the current elbow and knee guards worn by soldiers and known in the art.

Figure 23:
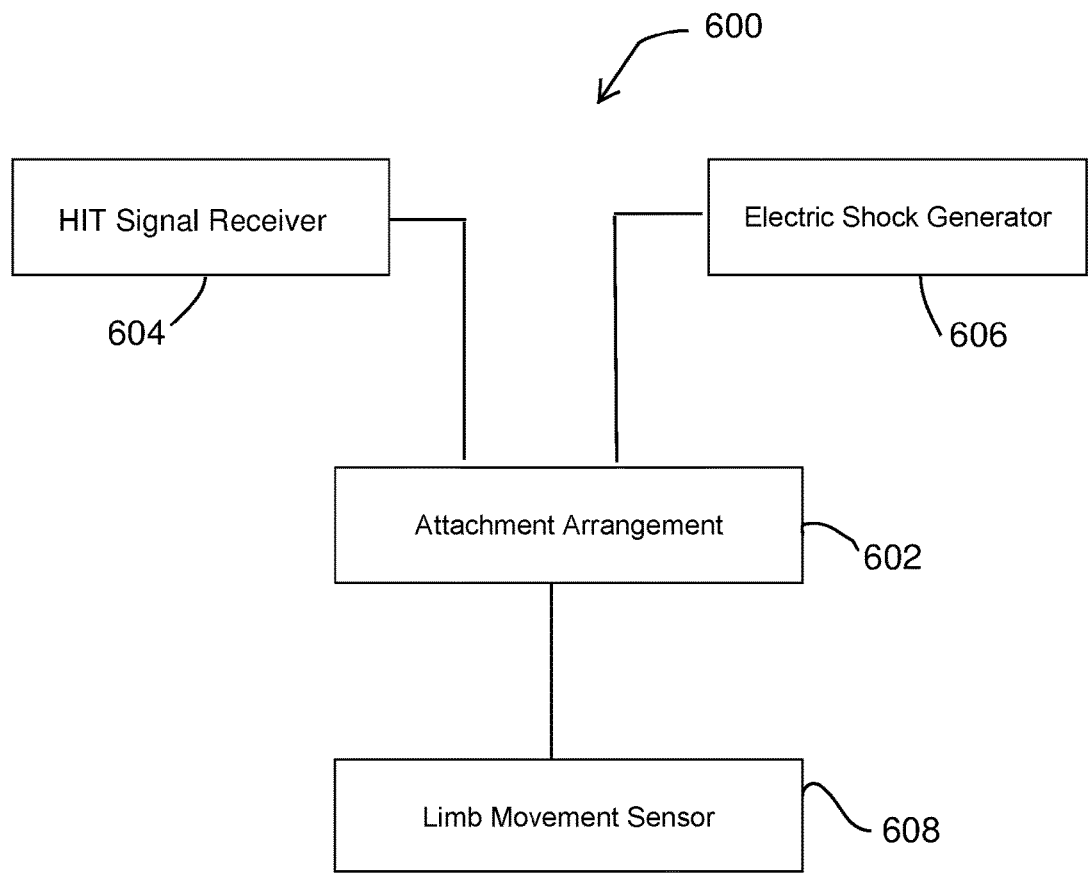
FIG. 23 schematically illustrates another limb locking device in accordance with the present teachings.

Turning to FIG. 23, another limb immobilization device according to the present teachings is illustrated and identified at reference character 600. The limb immobilization device 600 is shown to generally include an attachment arrangement 602 for securing the limb immobilization device to a user. The attachment arrangement 602 may include a plurality of straps or a brace.

The limb immobilization device 600 may further include a signal receiver 604 for indicating a hit to a limb of the user. The hit signal may be generated by any well known device.

The limb immobilization device 600 may further include an electric shock generator 606. The electric shock generator 606 may be operative to generate an electric shock and deliver the electric shock to the user in response to receipt of the hit signal. In this regard, the hit signal may be processed by a PCB (not shown). The electric shock may be sufficiently strong to encourage at least partial, involuntary immobilization of the limb.

The limb immobilization device 600 may further include a sensor 608. The sensor 608 may be operative to sense whether the limb is bent. In one specific application, the sensor 608 is a flex sensor that senses limb movement by a changing resistance according to an angle at which the limb is bent. A greater bending of the limb increases resistance which changes the reference voltage. This value may be transmitted to an electric current which, based on calibrated resistors, knows if the current bend angle is appropriate or not for administering a shock to the user. If the angle is such that a shock is appropriate, the device 600 may output a constant 3.5 v to the PCB, which checks the injured state of the associated limb and delivers a shock as appropriate to the user. One suitable flex sensor is commercially available from Flexpoint Sensor Systems Inc.

Alternatively, the sensor 608 may be operative to sense movement of the limb by sensing articulation of a corresponding joint of the user. For example, the device 600 may utilize a rotary sensor (changes voltage based on the angle of rotation), force detection sensor, or potentially others for alternate designs. Such sensors would work in a similar manner to that described above but simply detect the limb movement in a different way. As discussed, the device 600 may be operative to deliver a further electrical shock to the user with the electric shock generator 606 in response to sensed bending of the limb or sensed movement of the limb after the initial shock. Any further sensed bending or movement of the limb may result in continued shocking of the user. The continued shocking may increase in strength.

A system of the present teachings may include a plurality of limb attachments that simulate injuries by applying an electric shock when a limb is hot or a joint is articulated. Such a system allows a user to learn and practice physical maneuvers, such as firing a gun or rescuing an injured victim, which experiencing pain of a simulated injury. In addition, the electric shock and loss of immobility will create an intense stress response, helping to build the mental armor needed to excess under difficult situations.

It will now be understood that the present teachings provide a system for improving the realism of training scenarios by providing a painful hit consequence and injury simulation. The system may operate off any battlefield hit signal to enhance the realism and immersion of a wearer's training exercise.

The foregoing description of the embodiment(s) has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. One or more example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. A limb immobilization device for a battle simulation system comprising:
   an articulable joint;
   a sensor for sensing articulation of a corresponding joint of a user;
   a receiver for receiving a signal indicative of a hit to a limb of the user; and
   an electric shock generator operative to generate an electric shock and deliver the electric shock to the user upon both (1) receipt of the signal; and (2) a sensed articulation of the joint of the user,
   wherein a user's fear of electric shock administration is operative to make the user voluntarily immobilize the limb.

2. The limb immobilization device of claim 1, wherein the limb immobilization device is operative in a first mode to allow free movement of the limb of a user and operative in a second mode to at least partially restrict movement of the limb in response to receipt of the control signal.

3. The limb immobilization device of claim 1, wherein the limb immobilization device further includes a brace arrangement for attachment to the user.

4. The limb immobilization device of claim 3, wherein the brace arrangement includes a first brace for attachment to the user on a first side of a joint and a second brace for attachment to the user on a second side of the joint.

5. The limb immobilization device of claim 1, wherein the limb immobilization device further includes a sensor for sensing movement of the limb.

6. The limb immobilization device of claim 5, wherein the electric shock generator is operative to deliver a further shock to the user upon sensing of movement of the limb by the sensor.

7. The limb immobilization device of claim 5, wherein the sensor senses movement of the limb by sensing articulation of a corresponding joint of the user.

8. An immobilization device for a battlefield simulation system comprising:
   an attachment arrangement for securing the immobilization device to a user;
   a sensor for sensing articulation of a joint of the user;
   a receiver for receiving a signal indicative of a hit to a limb of the user; and
   an electric shock generator operative to generate an electric shock and deliver the electric shock to the user upon both (1) receipt of the signal; and (2) a sensed articulation of the joint of the user.

9. The immobilization device of claim 8, wherein a user fear of electric shock administration is operative to make the user voluntarily immobilize a limb.

10. The immobilization device of claim 8, wherein the electric shock generator is operative to deliver a further shock to the user upon sensing of movement of the limb by the sensor.

11. A method of simulating a battle, the method comprising:
    providing a limb immobilization device including a sensor for sensing articulation of a corresponding joint of a user; and
    a receiver for receiving a signal indicative of a hit to a limb of a user;
    attaching the limb immobilization device to the user;
    receiving a control signal by the limb immobilization device in response to a simulated hit to the limb; and
    at least partially immobilizing the limb in response to both receipt of the control signal and sensed articulation of the joint of the user,
    wherein a user fear of electric shock administration is operative to make the user voluntarily immobilize the limb.

12. The method of claim 11, wherein attaching the limb immobilization device to a user includes securing a first brace to the user on a first side of a joint and securing a second brace to the user on a second side of the joint.

13. The method of claim 11, further comprising operating the limb immobilization device in a first mode to allow free movement of the limb of the user and operating the limb immobilization device in a second mode to restrict movement of the limb in response to receipt of the control signal.

14. The method of claim 11, further comprising sensing movement of the limb and delivering a further electric shock to the user in response to sensed movement of the limb.

15. The method of claim 11, wherein sensing movement of the limb includes sensing articulation of a corresponding joint of the user.

16. The method of claim 15, further comprising increasing a strength of the electric shock in response to continued movement of the limb.

* * * * *